(12) United States Patent
Mohammed et al.

(10) Patent No.: US 10,087,355 B2
(45) Date of Patent: Oct. 2, 2018

(54) OIL-BASED DRILLING FLUIDS CONTAINING AN ALKALINE-EARTH DIAMONDOID COMPOUND AS RHEOLOGY MODIFIER

(71) Applicants: Saudi Arabian Oil Company, Dhahran (SA); Durham University, Durham (GB); M-I Drilling Fluids U.K. Limited, Westhill, Scotland (GB)

(72) Inventors: Musarrat H. Mohammed, Glasgow (GB); Hugh Christopher Greenwell, County Durham (GB); Manohara Gudiyor Veerabhadrappa, Durham (GB); John Adrian Hall, Dhahran (SA); Gasan Selman Alabedi, Cheshire (GB); Andrew Whiting, Durham (GB); Michael Hayward Hodder, Aberdeen (GB)

(73) Assignees: Saudi Arabian Oil Company, Dhahran (SA); Durham University, Durham (GB); M-I Drilling Fluids U.K. Limited, Westhill (GB)

( * ) Notice: Subject to any disclaimer, the term of this patent is extended or adjusted under 35 U.S.C. 154(b) by 0 days.

(21) Appl. No.: 15/449,347

(22) Filed: Mar. 3, 2017

(65) Prior Publication Data

US 2017/0267910 A1    Sep. 21, 2017

Related U.S. Application Data

(60) Provisional application No. 62/309,662, filed on Mar. 17, 2016.

(51) Int. Cl.
*E21B 1/00* (2006.01)
*C09K 8/32* (2006.01)
(Continued)

(52) U.S. Cl.
CPC ............... *C09K 8/32* (2013.01); *C07C 51/60* (2013.01); *C09K 8/34* (2013.01); *C09K 8/82* (2013.01);
(Continued)

(58) Field of Classification Search
CPC ... C09K 8/32; C09K 8/34; C09K 8/82; C09K 8/487; C09K 2208/10; C09K 2208/28; C07C 51/60; C07C 2103/74
(Continued)

(56) References Cited

U.S. PATENT DOCUMENTS 3,342,880 A   9/1967   Reinhardt
3,671,432 A   6/1972   Peters et al.
(Continued)

FOREIGN PATENT DOCUMENTS

CA    2594060 A1   6/2006
EP    1419817 A1   5/2004
(Continued)

OTHER PUBLICATIONS

Moorhead-Rosenberg et al., "A Rapid Microwave-Assisted Solvothermal Approach to Lower-Valent Transition Metal Oxides", Inorg. Chem., 2013, 52, 13087-13093, American Chemical Society.
(Continued)

*Primary Examiner* — Silvana C Runyan
(74) *Attorney, Agent, or Firm* — Dinsmore & Shohl LLP

(57) ABSTRACT

An oil-based drilling fluid and method of preparing an oil-based drilling fluid are disclosed. The oil-based drilling fluid comprising a base oil continuous phase, an aqueous discontinuous phase, and at least one rheology modifier. The at least one rheology modifier including an alkaline-earth diamondoid compound. The method of preparing the oil-based drilling fluid including mixing a base oil, at least one emulsifier, and at least one wetting agent to form a first
(Continued)

mixture, adding and mixing at least one rheology modifier into the first mixture to form a second mixture, adding and mixing at least one fluid-loss control additive into the second mixture to form a third mixture, adding and mixing a brine solution into the third mixture to form a fourth mixture, and adding and mixing a weighting additive into the fourth mixture to form the oil-based drilling fluid.

19 Claims, 8 Drawing Sheets

(51) Int. Cl.
  *C07C 51/60*  (2006.01)
  *C09K 8/34*  (2006.01)
  *C09K 8/82*  (2006.01)
  *C09K 8/487*  (2006.01)

(52) U.S. Cl.
  CPC .......... C07C 2103/74 (2013.01); C09K 8/487 (2013.01); C09K 2208/10 (2013.01); C09K 2208/28 (2013.01); E21B 1/00 (2013.01)

(58) Field of Classification Search
  USPC .......................................................... 175/65
  See application file for complete search history.

(56) References Cited

U.S. PATENT DOCUMENTS

| | | | |
|---|---|---|---|
| 4,021,371 A | 5/1977 | Petro et al. | |
| 4,419,222 A | 12/1983 | Grenoble et al. | |
| 4,774,212 A | 9/1988 | Drezdon | |
| 4,952,748 A * | 8/1990 | Alexander | C10G 21/00 208/334 |
| 4,956,481 A | 9/1990 | Gillaspey et al. | |
| 5,021,184 A | 6/1991 | Gillaspey et al. | |
| 5,073,532 A | 12/1991 | Domesle et al. | |
| 5,260,495 A | 11/1993 | Forkner | |
| 5,326,891 A | 7/1994 | Breuer et al. | |
| 5,399,329 A | 3/1995 | Schutz et al. | |
| 5,635,457 A * | 6/1997 | Van Slyke | C09K 8/34 507/103 |
| 5,883,041 A | 3/1999 | Pak et al. | |
| 6,096,690 A * | 8/2000 | Wittenbrink | C09K 8/34 208/14 |
| 6,323,270 B1 | 11/2001 | Ishida | |
| 6,410,635 B1 | 6/2002 | Kaylo et al. | |
| 6,429,314 B1 | 8/2002 | Ishii et al. | |
| 7,098,366 B2 | 8/2006 | Sigl et al. | |
| 7,129,287 B1 | 10/2006 | Lee et al. | |
| 7,557,063 B2 | 7/2009 | Hagemeyer et al. | |
| 7,582,202 B2 | 9/2009 | Jones et al. | |
| 7,918,935 B2 | 4/2011 | Park et al. | |
| 8,034,867 B2 | 10/2011 | Abarca et al. | |
| 8,088,349 B2 | 1/2012 | Duan et al. | |
| 8,158,843 B2 | 4/2012 | Song et al. | |
| 8,613,900 B2 | 12/2013 | Frei et al. | |
| 8,652,994 B2 | 2/2014 | Li et al. | |
| 2002/0110520 A1 | 8/2002 | Stamires et al. | |
| 2008/0108498 A1 | 5/2008 | Duan et al. | |
| 2008/0207801 A1 | 8/2008 | Ton-That et al. | |
| 2010/0279848 A1 | 11/2010 | Iyi et al. | |
| 2011/0237430 A1 | 9/2011 | Zhang et al. | |
| 2011/0248314 A1 | 10/2011 | Takei et al. | |
| 2012/0058739 A1 | 3/2012 | McKinzie, III et al. | |
| 2012/0258857 A1 | 10/2012 | Pham et al. | |
| 2012/0312344 A1 | 12/2012 | Delorme | |
| 2012/0322694 A1* | 12/2012 | Monteiro | C09K 8/032 507/105 |
| 2013/0116351 A1 | 5/2013 | Querner et al. | |
| 2013/0143731 A1 | 6/2013 | Li et al. | |
| 2013/0172642 A1 | 7/2013 | Behrens et al. | |
| 2013/0260990 A1 | 10/2013 | Kwon et al. | |
| 2014/0113196 A1 | 4/2014 | Balaya et al. | |
| 2015/0027710 A1 | 1/2015 | Miller | |
| 2017/0029375 A1 | 2/2017 | Harichian et al. | |
| 2017/0266642 A1 | 9/2017 | Veerabhadrappa et al. | |
| 2017/0267620 A1 | 9/2017 | Veerabhadrappa et al. | |
| 2017/0267623 A1 | 9/2017 | Veerabhadrappa et al. | |

FOREIGN PATENT DOCUMENTS

| | | |
|---|---|---|
| EP | 1952885 A1 | 8/2008 |
| EP | 2263976 A1 | 12/2010 |
| WO | 0224756 A2 | 3/2002 |
| WO | 2013007993 A2 | 1/2013 |
| WO | 2013072197 A1 | 5/2013 |
| WO | 2014037378 A1 | 3/2014 |
| WO | 2014052510 A1 | 4/2014 |
| WO | 2014080428 A1 | 5/2014 |

OTHER PUBLICATIONS

Schwertfeger et al., "Diamonds are a Chemist's Best Friend: Diamondoid Chemistry Beyond Adamantane", Angew. Chem. Int. Ed., 2008, 47, 1022-1036, Wiley-VCH GmbH & Co.

Schwertmann et al., "The Formation of Green Rust and Its Transformation to Lepidocrocite", Clay Minerals, 1994, 29, 87-92, The Mineralogical Society.

Singoredjo et al., "Alumina Supported Manganese Oxides for the Low-Temperature Selective Catalytic Reduction of Nitric Oxide with Ammonia", Applied Catalysis B: Environmental, 1992, 1, 297-316, Elsevier Science Publishers B.V.

Spaldin et al., "The Renaissance of Magnetoelectric Multiferroics", Science, 2005, 309, 391-392, AAAS.

Spyrou et al., "Towards Novel Multifunctional Pillared Nanostructures: Effective Intercalation of Adamantylamine in Graphene Oxide and Smectite Clays", Adv. Fund. Mater, 2014, 24, 2841-5850, Wiley-VCH Verlag GmbH & Co.

Stankic et al., "Size-Dependent Optical Properties of MgO Nanocubes", Angew. Chem. Int. Ed., 2005, 44, 4917-4920, Wiley-VCH Verlag GmbH & Co.

Stein et al., "Salt-Gel Synthesis of Porous Transition-Metal Oxides", Chem. Mater., 1995, 7, 304-313, American Chemical Society.

Tao et al., "Synthesis and Characterization of Layered Double Hydroxides with a High Aspect Ratio", Journal of Solid State Chemistry, 2006, 179, 708-715, Elsevier Inc.

Tian et al., "Manganese Oxide Mesoporous Structures: Mixed-Valent Semiconducting Catalysts", Science, 1997, 276, 926-930.

Tokura et al., "Orbital Physics in Transition-Metal Oxides", Science, 2000, 288, 462-468.

Vidal-Michel et al., "Effect of Crystal Size on the Oxidative Dehydrogenation of Butane on V/MgO Catalysts", Journal of Catalysis, 2004, 221, 127-136, Elsevier Inc.

Walia et al., "Transition Metal Oxides—Thermoelectric Properties", Progress in Materials Science, 2013, 58, 1443-1489, Elsevier Ltd.

Wang et al., "Electronics and Optoelectronics of Two-Dimensional Transition Metal Dichalcogenides", Nature Nanotechnology, 2012, 7, 699-712, Macmilan Publishers.

Wang et al., "CO2 Capture by Solid Adsorbents and Their Applications: Current Status and New Trends", Energy Environ. Sci., 2011, 4, 42-55, The Royal Society of Chemistry.

Westerhaus et al., "Heterogenized Cobalt Oxide Catalysts for Nitroarene Reduction by Pyrolysis of Molecularly Defined Complexes", Nature Chemistry, 2013, 5, 537-543.

Xie et al., "Low-Temperature Oxidation of CO Catalysed by Co3O4 Nanorods", Nature, 2009, 458, 746-749, Macmilian Publishers Limited.

Xu et al., "Surface Area and Thermal Stability Effect of the MgO Supported Catalysts for the Synthesis of Carbon Nanotubes", Journal of Materials Chemistry, 2008, 18, 5738-5745, The Royal Society of Chemistry.

Zhang et al., "Synthesis and Transformation of Linear Adamantane Assemblies Inside Carbon Nanotubes", ACS Nano, 6:10, 8674-8683.

(56) References Cited

OTHER PUBLICATIONS

Zhang et al., "Hydrogen Production via the Direct Cracking of Methane Over Silica-Supported Nickel Catalysts", Applied Catalysts A: General, 1998, 167, 161-172, Elsevier B.V.
Zhuang et al., "Comparative Study on the use of Cationic-Nonionic-Organo-Montmorillonite in Oil-Based Drilling Fluids", Applied Clay Science, 2015, 116-117, 257-262, Elsevier B.V.
International Search Report and Written Opinion pertaining to PCT/US2017/021135 dated Jun. 12, 2017.
International Search Report and Written Opinion pertaining to PCT/US2017/022427 dated Jun. 12, 2017.
International Search Report and Written Opinion pertaining to PCT/US2017/021478 dated May 29, 2017.
Lu et al., "Sheet-like and Fusiform CuO Nanostructures Grown on Graphene by Rapid Microwave Heating for High Li-Ion Storage Capacities", J. Mater. Chem., 2011, 21, 17916.
Huang et al., "Controllable Preparation of Nano-MgO and Investigation of its Bactericidal Properties", Journal of Inorganic Biochemistry, 2005, 99, 986-996.
Chen et al., "Cu2(ATC) 6H2O: Design of Open Metal Sites in Porous Metal-Organic Crystals (ATC: 1,3,5,70Adamantane Tetracarboxylate", J. Am. Chem. Soc., 2000, 122, 11559-11560.
Kim et al., "Assembly of Metal-Organic Frameworks from Large Organic and Inorganic Secondary Building Units: New Examples and Simplifying Principles for Complex Structures", J. Am. Chem. Soc., 2001, 123, 8239-8247.
International Search Report dated Jul. 13, 2017, pertaining to PCT/US2017/021550, filed Mar. 9, 2017, 8 pages.
Written Opinion dated Jul. 13, 2017, pertaining to PCT/US2017/021550, filed Mar. 9, 2017, 13 pages.
U. Costantino, et al., Preparation and characterization of hydrotalcite/carboxyadamantane intercalation compounds as fillers of polymeric nanocomposites, Journal of Materials Chemistry, vol. 17, No. 11, Dec. 22, 2006, pp. 1079-1086.
Goh, et al., Application of layered double hydroxides for removal of oxyanions: A review, Water Research, Elsevier, vol. 42, No. 6-7, Nov. 7, 2007, pp. 1343-1368, Amsterdam, Netherlands.
Kanezaki, Unexchangeable Interlayer Anions: Synthesis and Characterization of Zn/Al- and Mg/A1-Layered Double Hydroxides with Interlayer Alizarin red S, Journal of Inclusion Phenomena and Macrocyclic Chemistry, Jun. 1, 2003, pp. 89-95, https://rd.springer.com.
Crepaldi, et al., Sorption of terephthalate anions by calcined and uncalcined hydrotalcite-like compounds, Colloids and Surfaces A: Physicochem. Eng. Aspects 211, vol. 211, No. 2-3, Jun. 4, 2002, pp. 103-114, Amsterdam, Netherlands.
Sabbar, et al., Probing the interaction between di- and tri-functionalized carboxy-phosphonic acid and LDH layer structure, Journal of Physics and Chemistry of Solids, Pergamon Press, vol. 67, No. 11, Sep. 6, 2006, pp. 2419-2429, London, England.
Lima, et al., Characterization of basic catalysts by the use of nitromethane as NMR probe molecule and reactant, Journal of Cataly, Academic Press, vol. 223, No. 1, Feb. 20, 2004, pp. 28-35, USA.
Khan et al., The intercalation of bicyclic and tricyclic carboxylates into layered double hydroxides, Journal of Solid State Chemistry, vol. 183, No. 12, Sep. 30, 2010, pp. 2877-2885, USA.
Abdo et al., "Clay Nanoparticles Modified Drilling Fluids for Drilling of Deep Hydrocarbon Wells", Applied Clay Science, 2013, 86, 76-82, Elsevier B.V.
Abdou et al., "Evaluation of Egyptian Bentonite and Nano-Bentonite as Drilling Mud", Egyptian Journal of Petroleum, 2013, 22, 53-59, Egyptian Petroleum Research Institute.
Alvarado et al., "Preparation and Characterization of MgO Powders Obtained from Different Magnesium Salts and the Mineral Dolomite", Polyhedron, 2000, 19, 2345-2351, Elsevier Science B.V.
Baltes et al., "Synthesis of Supported Transition Metal Oxide Catalysts by the Designed Deposition of Acetylacetonate Complexes", Langmuir, 1999, 15, 5841-5845, American Chemical Society.

Bednorz et al., "Possible High Tc Superconductivity in the Ba—La—Cu—O System", Condensed Matter, 1986, 64, 189-193, Springer-Verlag.
Bernholc et al., "Bronsted Acid Sites in Transition Metal Oxide Catalysts: Modeling of Structure, Acid Strengths, and Support Effects", J. Phys. Chem., 1987, 91, 1526-1530, American Chemical Society.
Cao et al., "Ultra-High Capacity Lithium-Ion Batteries with Hierarchical CoO Nanowire Clusters as Binder Free Electrodes", Advanced Functional Materials, 2015, 25, 1082-1089, Wiley-VCH Verlag GmbH & Co.
Cao et al., "Mg(OH)2 Complex Nanostructures with Superhydrophobicity and Flame Retardant Effects", J. Phys. Chem., 2010, 114, 17362-17368, American Chemical Society.
Choudary et al., "Benzylation of Aromatic Compounds with Different Crystallites of Mgo", Journal of American Chemical Society, 2003, 125, 2020-2021, American Chemical Society.
Di Cosimo et al., "Basic Catalysis on MgO: Generation, Characterization and Catalytic Properties of Active Sites", Catalysis, 2014, 26, 1-28.
Gardolinski et al., "Grafted Organic Derivatives of Kaolinite: I. Synthesis, Chemical and Rheological Characterization", Clay Minerals, 2005, 40, 537-546, The Mineralogical Society.
Guo et al., "A Comprehensive Review on Synthesis Methods for Transition-Metal Oxide Nanostructures", CrystEngComm, 2015, 17, 3551-3585, The Royal Society of Chemistry.
Haber, Jerzy, "Catalysis by Transition Metal Oxides", ACS Symposium Series, Washington D.C., 1985, Grasselli and Brazdil: Solid State Chemistry in Catalysis, American Chemical Society.
Hermoso et al., "Influence of Viscosity Modifier Nature and Concentration on the Viscous Flow Behaviour of Oil-Based Drilling Fluids at High Pressure", Applied Clay Science, 2014, 87, 14-21, Elsevier B.V.
Hsueh et al., "Preparation and Properties of LDHs/Epoxy Nanocomposites", Polymer, 2003, 44, 5275-5283, Elsevier Ltd.
Huang et al., "Removal of NO by Reversible Adsorption on Fe—Mn Based Transition Metal Oxides", Langmuir, 2001, 17, 4997-5003, American Chemical Society.
Jagadeesh et al., "Selective Oxidation of Alcohols to Esters Using Heterogeneous Co3O4—N@C Catalysts Under Mild Conditions", Journal of the American Chemical Society, 2013, 135, 10776-10782, American Chemical Society.
Jiancheng et al., "A New Type of Whole Oil-Based Drilling Fluid", Petrol. Explor. Develop., 2014, 41(4), 538-544, Elsevier B.V.
Johnson, Mark, "Spintronics", J. Phys. Chem. B, 2005, 109, 14278-14291, American Chemical Society.
Kelkar et al., "Mi-, Mg- and Co-Containing Hydrotalcite-Like Materials with a Sheet-Like Morphology: Synthesis and Characterization", Microporous Materials, 1997, 10, 163-172, Elsevier Science B.V.
Krishnamoorthy et al., "Catalytic Oxidation of 1,2-Dichlorobenzene Over Supported Transition Metal Oxides", Journal of Catalysis, 2000, 193, 264-272, Academic Press.
Kumar et al., "Sonochmical Synthesis and Characterization of Nanometer-Size Transition Metal Oxides from Metal Acetates", Chem .Mater., 2000, 12, 2301-2305, American Chemical Society.
Kumar et al., "Effect of MgO Nanoparticles on Ionic Conductivity and Electrochemical Properties of Nanocomposite Polymer Electrolyte", Journal of Membrane Science, 2007, 300, 104-110, Elsevier B.V.
Lebaron et al., "Polymer-Layered Silicate Nanocomposites: An Overview", Applied Clay Science, 1999, 15, 11-29, Elsevier Science B.V.
Li et al., "Electroreduction of Carbon Monoxide to Liquid Fuel on Oxide-Derived Nanocrystalline Copper", Nature, 2014, 508, 504-507, MacMilan Publishers.
Li et al., "Mg(OH)2@reduced Graphene Oxide Composite for Removal of Dyes From Water", Journal of Materials Chemistry, 2011, 21, 13765-13768, The Royal Society of Chemistry.
Li et al., "Preparation of Nanocomposites of Metals, Metal Oxides, and Carbon Nanotubes via Self-Assembly", J. Am. Chem. Soc., 2007, 129, 9401-9409, American Chemical Society.

(56) References Cited

OTHER PUBLICATIONS

Li et al., "Positively Charged Nanosheets Derived via Total Delamination of Layered Double Hydroxides", Chem. Mater., 2005, 17, 4386-4391, American Chemical Society.
Li et al., "Stable Platinum Nanoparticles on Specific MgAl2O4 Spinal Facets at High Temperatures in Oxidizing Atmospheres", Nature Communications, 2013, DOI: 10.1038/ncomms3481, MacMilan Publishers Limited.
Liu et al., "Layered Double Hydroxide Nano- and Microstructures Grown Directly on Metal Substrates and Their Calcined Products for Application as Li-Ion Battery Electrodes", Advanced Functional Materials, 2008, 18, 1448-1458, Wiley-VCH Verlag GmbH & Co.
Liu et al., "Gold-Catalyzed Direct Hydrogenative Coupling of Nitroarenes to Synthesize Aromatic Azo Compounds", Angew. Chem., 2014, 126, 7754-7758, Wiley-VCH Verlag GmbH & Co.
Liu et al., "Selective and Controlled Synthesis of a- and b-Cobalt Hydroxides in Highly Developed Hexagonal Platelets", J. Am. Chem. Soc., 2005, 127, 13869-13874, American Chemical Society.
Ma et al., "Metal-Organic Framework Derived Hybrd Co3O4-Carbon Porous Nanowire Arrays as Reversible Oxygen Evolution Electrodes", J. Am. Chem. Soc., 2014, 136, 13925-13931, American Chemical Society.
Makhluf et al., "Microwave-Assisted Synthesis of Nanocrystalline MgO and Its Use as a Bacteriocide", Adv. Funct. Mater, 2005, 15, 1708-1715, Wiley-VCH Verlag GmbH.
Mishra et al., "Effect of Nano-Mg(OH)2 on the Mechanical and Flame-Retarding Properties of Polypropylene Composites", Journal of Applied Polymer Science, 2004, 94, 116-122, Wiley Periodicals, Inc.
Nethravathi et al., "Synthesis and Anion-Exchange Reactions of a New Anionic Clay a-Magnesium Hydroxide", Journal of Colloid and Interface Science, 2011, 354, 793-797, Elsevier Inc.
Newman et al., "Comparative Study of Some Layered Hydroxide Salts Containing Exchangeable Interlayer Anions", Journal of Solid State Chemistry, 1999, 148, 26-40, Academic Press.
Nielsen et al., "Delamination, Synthesis, Crystal Structure and Thermal Properties of the Layered Metal-Organic Compound Zn(C12H14O4)", J. Mater. Chem., 2008, 18, 1002-1007, The Royal Society of Chemistry.
Ning et al., "Gas-Hydrate Formation, Agglomeration and Inhibition in Oil-Based Drilling Fluids for Deep-Water Drilling", Journal of Natural Gas Chemistry, 2010, 19, 234-240, Elsevier.
Oswald et al., "Bivalent Metal Hydroxides", Preparation and Crystal Growth of Materials with Layered Structures, 1977, 71-140.
Park et al., "Synthesis and Characterization of Al(OH)3/Polystyrene Nanocomposite Latex Particles by Emulsion Polymerization", Macromol. Symp., 2007, 247-250.
Pham et al., "A Silica-Supported Iron Oxide Catalyst Capable of Activating Hydrogen Peroxide at Neutral pH Values", Environ. Sci. Technol., 2009, 43, 8930-8935, American Chemical Society.
Pupovac et al., "Cu/MgAl2O4 as Bifunctional Catalyst for Aldol Condensation of 5-Hydroxymethylfurfural and Selective Transfer Hydrogenation", ChemSusChem, 2013, 6, 2103-2110.
Qian et al., "Micropore Modification of Zeolites with Transition-Metal Oxides", Colloids and Surfaces A: Physiochemical and Engineering Aspects, 2001, 180, 311-316, Elsevier Science B.V.
Rajamathi et al., "The Many Ways of Making Anionic Clays", Proc. Indian Acad. Sci. (Chem. Sci.), 2001, 5 & 6, 671-680, Indian Academy of Sciences.
Ramirez, A.P., "Colassal Magnetoresistance", J. Phys.: Condens. Matter, 1997, 9, 8171-8199, IOP Publishing Ltd.
Rao et al., "Synthesis of Complex Metal Oxides by Novel Routes", Acc. Chem. Res., 1987, 20, 228-235, American Chemical Society.
Rao, C.N.R., "Transition Metal Oxides", Annu. Rev. Phys. Chem., 1989, 40, 291-326, Annual Reviews Inc.
Raveau, B., "Transition Metal Oxides: Promising Functional Materials", Journal of the European Ceramic Society, 2005, 25, 1965-1969, Elsevier Ltd.

Reddy et al., "Metal Oxides and Oxysalts as Anode Materials for Li Ion Batteries", Chem. Rev. 2013, 113, 5364-5457, American Chemical Society.
International Search Report dated Jul. 13, 2017, pertaining to PCT/US2017/022485, filed Mar. 15, 2017, 7 pages.
Written Opinion dated Jul. 13, 2017, pertaining to PCT/US2017/022485, filed Mar. 15, 2017, 11 pages.
Cavani et al., Hydrotalcite-Type Anionic Clays: Preparation, Properties and Applications, Catalysis Today, vol. 11, 1991, 173-301, Elsevier Science Publishers B.V.
Chang, et al., "Ca-Rich Ca—Al—Oxide, High-Temperature-Stable Sorbents Prepared from Hydrotalcite Precursors: Synthesis, Characterization, and CO2 Capture Capacity", ChemSusChem, 2011, vol. 4, 1844-1851, Wiley-VCH.
Chen, et al., "Preparation and Characterization of Flexible Asymmetric Supercapacitors Based on Transition-Metal-Oxide Nanowire/Single-Walled Carbon Nanotube Hybrid Thin-Film Electrodes", ACSNano, 2010, vol. 4, No. 8, 4403-4411, American Chemical Society.
Damodara et al., "Copper Nanoparticles from Copper Aluminum Hydrotalcite: An Efficient Catalyst for Acceptor- and Oxidant-Free Dehydrogenation of Amines and Alcohols", Adv. Synth. Catal., 2014, vol. 356, 189-198, Wiley-VCH.
Del Arco et al., "Release studies of different NSAIDS encapsulated in Mg, Al, Fe-hydrotalcites" Applied Clay Science, vol. 42, 2009, 538-544, Elsevier B.V.
Ding, et al., "Equilibria and kinetics of CO2 absorption on hydrotalcite adsorbent" Chemical Engineering Science, 2000, vol. 55, 3461-3474, Elsevier Science Ltd.
Gardolinski et al., "Grafted organic derivatives of kaolinite: II. Intercalation of primary n-alkylamines and delamination", Clay Minerals, 2005, vol. 40, 547-556, The Mineralogical Society.
Itoh, et al., Nanoscale Metal Oxide Particles as Chemical Reagents. Intrinsic Effects of Particle Size on Hydroxyl Content and on Reactivity and Acid/Base Properties of Ultrafine Magnesium Oxide, Chem. Mater. 1993, vol. 5, 71-77, American Chemical Society.
Khan, et al., "Intercalation chemistry of layered double hydroxides: recent developments and applications", Journal of Materials Chemistry, 2002, vol. 12, 3191-3198, The Royal Society of Chemistry.
Kumar, et al., "Sonochemical Synthesis and Characterization of Nanometer-Size Transition Metal Oxides from Metal Acetates" Chem. Mater. 2000, vol. 12, 2301-2405, American Chemical Society.
Kumbhar, et al., Reduction of Aromatic Nitro Compounds with Hydrazine Hydrate in the Presence of the Iron(III) Oxide-MgO Catalyst Prepared from a Mg—Fe Hydrotalcite Prescursor, Tetrahedron Letters, 1998, vol. 39, 2573-2574, Elsevier Science Ltd.
Kumbhar, et al., Mg—Fe Hydrotalcite as a Catalyst for the Reduction of Aromatic Nitro Compounds with Hydrazine Hydrate, Journal of Catalysis, 2000, vol. 191, 467-473, Academic Press.
Li, et al., "Mg(OH)2@reduced graphene oxide composite for removal of dyes from water", Journal of Materials Chemistry, 2011, vol. 21, 13765-13768, The Royal Society of Chemistry.
Meyn et al., "Anion-Exchange Reactions of Layered Double Hydroxides" Inorg. Chem. 1990, vol. 29, 5201-5207, American Chemical Society.
Miyata, Shigeo, "Physico-Chemical Properties of Synthetic Hydrotalcites in Relation to Composition", Clays and Clay Minerals, 1980, vol. 28, No. 1, 50-56, The Clay Minerals Society.
Mulukutla, C. Detellier, "Thermally activated Mg, Fe layered double hydroxide as reductant for nitric oxide", Journal of Materials Science Letters 1996, vol. 15, 797-799, Chapman & Hall.
Nethrvathi, et al., Cobalt Hydroxide/Oxide Hexagonal Ring-Graphene Hybrids through Chemical Etching of Metal Hydroxide Platelets by Graphene Oxide: Energy Storage Applications, ASCNano, 2014, vol. 8, No. 3, 2755-2765, American Chemical Society.
Poizot et al., Nano-sized transition-metal oxides as negative-electrode materials for lithium-ion batteries, Nature, 2000, vol. 407, pp. 496-499, Macmillan Magazines Ltd.
Prasanna, et al., Chromate uptake characteristics of pristine layered double hydroxides of Mg with Al, Solid State Sciences, 2008, vol. 10, 260-266, Elsevier Masson SAS.

(56) References Cited

OTHER PUBLICATIONS

Reichle, Walter T., "Catalytic Reactions by Thermally Activated Anionic Clay Minerals" Journal of Catalysis, 1985, vol. 94, 547-557, Academic Press, Inc.

Shukla, et al., "Stabilized a-Ni(OH)2 as Electrode Material for Alkaline Secondary Cells", J. Electrochem Soc., 1994, vol. 141, No. 11, 2956-2959, The Electrochemical Society, Inc.

Tao et al., "A redox-stable efficient anode for solid-oxide fuel cells" Nature Materials, 2003, vol. 2, 320-323, Nature Publishing Group.

Wang, et al., "Synthesis of high-temperature CO2 adsorbents from organo-layered double hydroxides with markedly improved CO2 capture capacity" the Royal Society of Chemistry, 2012, vol. 5, 7526-7530, Energy Environ. Sci.

White et al., Supported metal nanoparticles on porous materials. Methods and Applications; The Royal Society of Chemistry 2009, vol. 38, 481-494, Chemical Society Reviews.

Williams, et al., "Towards understanding, control and application of layered double hydroxide chemistry", Journal of Materials Chemistry, 2006, vol. 16, 3065-3074, Journal of Materials Chemistry.

Yao, et al., "Confined adamantane molecules assembled to one dimension in carbon nanontubes" Carbon, 2011, vol. 49, 1159-1166, Elsevier Ltd.

Yavuz, et al., "Markedly Improved CO2 Capture Efficiency and Stability of Gallium Substituted Hydrotalcites at Elevated Temperatures" Chem. Mater 2009, vol. 21, 3473-3475, American Chemical Society.

Zhao, et al., "Carbon Nanowire Made of a Long Lineal Carbon Chain Inserted Inside a Multiwalled Carbon Nanotube", Physical Review Letters, 2003, vol. 90, No. 18, 187401-1-187401-4, The American Physical Society.

Non-Final Office Action dated Jan. 5, 2018 pertaining to U.S. Appl. No. 15/453,106, filed Mar. 8, 2017.

Vittal, The Chemistry of Inorganic and Organometallic Compounds with Adamantane-Like Structures: Polyhedron, vol. 15, No. 10, pp. 1585-1642 (1996).

Non-Final Office Action dated Jan. 5, 2018 pertaining to U.S. Appl. No. 15/453,180, filed Mar. 8, 2017.

U.S. Non-Final Office Action dated May 25, 2018, pertaining to U.S. Appl. No. 15/449,207.

Office Action pertaining to U.S. Appl. No. 15/453,056 dated Jul. 10, 2018.

* cited by examiner

OIL-BASED DRILLING FLUIDS CONTAINING AN ALKALINE-EARTH DIAMONDOID COMPOUND AS RHEOLOGY MODIFIER

CROSS-REFERENCE TO RELATED APPLICATIONS

This application claims the benefit of U.S. provisional application Ser. No. 62/309,662 filed Mar. 17,2016.

BACKGROUND

Field

The present specification generally relates to drilling fluids for use in petroleum engineering and drilling methods incorporating the drilling fluids and, more specifically, to rheology modifiers for drilling fluids and associated drilling methods.

Abbreviations
- Å=Angstrom
- ACA=1-adamantane carboxylic acid
- AC=adamantane carboxylate
- AHR=after hot rolling
- ° C.=Degrees Celsius
- cm=centimeter ($10^{-2}$ meter)
- $cm^{-1}$=wavenumber
- cP=centipoise
- BHR=before hot rolling
- EDX=Energy-Dispersive X-Ray
- ES=electrical stability
- ° F.=Degrees Fahrenheit
- FL=fluid loss
- FWHM=full width at half maximum
- g=gram
- h=hours
- HRTEM=High-Resolution Transmission Electron Microscopy
- IR=Infrared
- lbf/100 ft$^2$=pounds force per hundred square feet (1 lbf/100 ft$^2$=0.4788 Pa)
- LDH=layered double hydroxide
- μm=micrometer ($10^{-6}$ meter)
- mL=milliliter ($10^{-3}$ liter)
- MPa=megapascal ($10^6$ Pascal)
- nm=nanometer ($10^{-9}$ meter)
- OBM=oil-based mud
- Pa=Pascal
- psi=pounds per square inch
- PV=plastic viscosity
- PXRD=Powder X-ray diffraction
- rpm=revolutions per minute
- s=second
- SEM=Scanning electron microscopy
- SG=specific gravity
- TEM=Transmission electron microscopy
- TGA=Thermogravimetric analysis
- TMO=Transition metal oxide
- V=volts
- YP=yield point
- wt. %=weight percent Technical Background Drilling fluids or drilling muds are compositions that are circulated through a wellbore to facilitate drilling operations while the wellbore is being drilled. In general, drilling fluids may facilitate the removal of drill cuttings from the wellbore, may cool and lubricate the drill bit, may aid in support of the drill pipe and drill bit, or may provide a hydrostatic head to maintain the integrity of the wellbore walls and prevent well blowouts. Specific drilling fluid systems are selected to optimize a drilling operation in accordance with the characteristics of a particular geological formation. For the drilling fluid or drilling mud to perform its functions, its optimum chemical and rheological properties must be controlled.

Oil-based muds (OBMs) used in drilling typically include: a base oil (or synthetic fluid) which make up a continuous phase of an emulsion; a aqueous solution such as a saline/water solution that makes up the discontinuous phase of the emulsion; optional emulsifiers; and other optional agents or additives for suspension, weight or density, oil-wetting, fluid loss or filtration control, and rheology modifiers. The rheology modifiers commonly include organophilic clays or organophilic lignites. An oil-based drilling fluid may commonly contain from about 50:50 to about 95:5 by volume continuous phase to discontinuous phase.

Drilling in deep wells is complicated by geological conditions that involve high pressures and high temperatures (HPHT). The industry-defined definition of HPHT conditions typically include a wellbore temperature greater than 300° F. (149° C.) and a wellbore pressure greater than 10,000 psi (68.9 MPa). Known drilling fluids typically contain clay-based rheology modifiers that are not suitable for HPHT drilling because they decompose under HPHT conditions. Thus, there are ongoing needs for drilling fluids and rheology modifiers for drilling fluids that are thermally stable under HPHT conditions and that have suitable rheological properties.

SUMMARY

According to some embodiments an oil-based drilling fluid is provided. The oil-based drilling fluid includes a base oil continuous phase, an aqueous discontinuous phase, and at least one rheology modifier. The at least one rheology modifier includes an alkaline-earth diamondoid compound.

According to some embodiments a method for preparing an oil-based drilling fluid is provided. The method includes mixing a base oil, at least one emulsifier, and at least one wetting agent to form a first mixture. Further, the method includes adding and mixing at least one rheology modifier into the first mixture to form a second mixture. The at least one rheology modifier includes an alkaline-earth diamondoid compound. Additionally, the method includes adding and mixing at least one fluid-loss control additive into the second mixture to form a third mixture. The method also includes adding and mixing a brine solution into the third mixture to form a fourth mixture. Finally, the method includes adding and mixing a weighting additive into the fourth mixture to form the oil-based drilling fluid.

According to some embodiments a method for drilling in a subterranean formation under high-pressure high-temperature conditions is provided. The method includes providing or using in the drilling of a wellbore into the subterranean formation an oil-based drilling fluid according to embodiments of this disclosure or an oil-based drilling fluid prepared according to the method of embodiments of this disclosure.

Additional features and advantages of the embodiments described herein will be set forth in the detailed description which follows, and in part will be readily apparent to those skilled in the art from that description or recognized by practicing the embodiments described herein, including the detailed description which follows, the claims, as well as the appended drawings.

It is to be understood that both the foregoing general description and the following detailed description describe various embodiments and are intended to provide an overview or framework for understanding the nature and character of the claimed subject matter. The accompanying drawings are included to provide a further understanding of the various embodiments, and are incorporated into and constitute a part of this specification. The drawings illustrate the various embodiments described herein, and together with the description serve to explain the principles and operations of the claimed subject matter.

DETAILED DESCRIPTION

Figure 1:
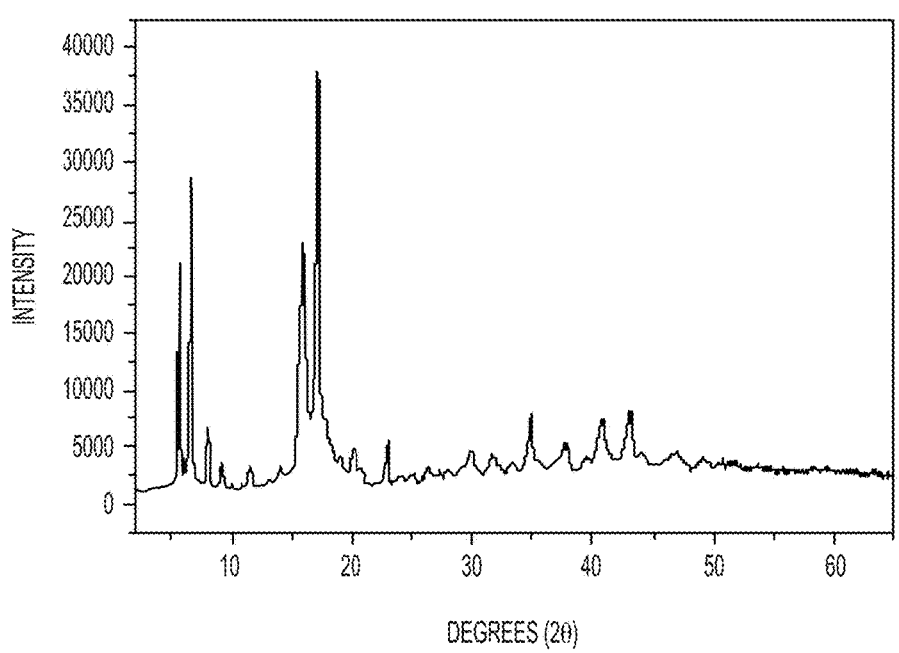
FIG. 1 is a powder x-ray diffraction (PXRD) pattern of a Mg(0.5)-AC magnesium adamantane carboxylate salt formed from Mg(OH)$_2$ and 1-adamantane carboxylic acid (ACA) with a 0.5:1 molar ratio of Mg$^{2+}$ to ACA.

Oil-based fluids according to various embodiments in this specification are described that have rheological properties, electrical stability after hot rolling, gel strength, and fluid-loss characteristics at 350° F. and pressure of 500 psi that render the oil-based drilling fluids suitable for use in high-pressure high-temperature (HPHT) conditions in wellbore operations. The oil-based fluids contain an alkaline-earth metal diamondoid compound as a rheology modifier. Methods for preparing the oil-based fluids, therefore, include adding the alkaline-earth metal diamondoid compound during a mixing procedure. Methods for drilling in a subterranean formation under high-pressure high-temperature conditions include using the oil-based drilling fluids containing the alkaline-earth metal diamondoid compound rheology modifier.

As used in this specification, the term "diamondoid" refers to any chemical compound containing at least one adamantane moiety. As used in this specification, the term "alkaline earth metal diamondoid compound" refers to compounds of magnesium, calcium, strontium, barium, or beryllium that additionally contain at least one adamantane moiety.

Embodiments of oil-based drilling fluids will now be described. Embodiments of methods for preparing the oil-based drilling fluids and of methods for drilling in a subterranean formation under high-pressure high-temperature conditions using the oil-based drilling fluids will be described subsequently.

Oil-based drilling fluids according to various embodiments may contain a base oil continuous phase, an aqueous discontinuous phase, and at least one rheology modifier. The at least one rheology modifier includes an alkaline-earth diamondoid compound.

The base oil continuous phase of the oil-based drilling fluids may be composed of a synthetic oil comprising an ester or olefin or may be a natural petroleum-derived product such as a diesel oil or a mineral oil. The synthetic oil or natural petroleum product may be composed of hydrocarbons such as n-paraffins, iso-paraffins, cyclic alkanes, branched alkanes, or mixtures thereof. The oil-based drilling fluid may contain from about 10.0 wt. % to 20.0 wt. % base oil, based on the total weight of the oil-based drilling fluid. In a further embodiment, the oil-based drilling fluid may contain from about 13.0 wt. % to 17.0 wt. % base oil, based on the total weight of the oil-based drilling fluid.

The aqueous discontinuous phase of the oil-based drilling fluid may include water and a salt source. In some embodiments, the aqueous discontinuous phase may be composed of a salt brine made up of water and a salt chosen from calcium chloride, calcium bromide, sodium chloride, sodium bromide, and combinations thereof, for example. The oil-based drilling fluid may contain from about 3.0 wt. % to about 6.0 wt. % aqueous discontinuous phase, based on the total weight of the oil-based drilling fluid. In some embodiments, the oil-based drilling fluid may have an oil-to-water ratio by volume of from 50:50 to 95:5, from 75:20 to 95:5, from 85:15 to 95:5, or from 90:10 to 95:5, for example. The oil-to-water ratio of the oil-based drilling fluid is the volumetric ratio calculated as Oil:water=base oil Saraline 185V+surfactant(s)+emulsifier(s)+wetting agent(s):(brine*0.64)+water. As the brine is 64% water by volume, 64% of the brine volume is included as water volume.

The oil-based drilling fluid contains at least one rheology modifier. The rheology modifier includes an alkaline-earth diamondoid compound. Rheology modifiers in general are components of the oil-based drilling fluid that adjust rheological properties of the oil-based drilling fluid such as viscosity, for example. Rheology modifiers may improve a drilling fluid's ability to remove cuttings from the wellbore and to suspend cuttings and weight materials during periods of non-circulation. The at least one rheology modifier may also include one or more rheology modifiers in addition to the alkaline-earth diamondoid compound. The additional rheology modifiers may be any compound known or determined to adjust the rheology of the oil-based drilling fluid in a manner more favorable to use of the oil-based drilling fluid in drilling operations at the temperatures and pressures at which the drilling operations are carried out. Examples of suitable additional rheology modifiers include clays or polymers, for example, organophilic clays such as hectorites, bentonites, sepiolites, attapulgites, and mixtures thereof. Organophilic clays are clay minerals, the surfaces of which have been coated with a chemical to make them oil-dispersible. In some embodiments, the oil-based drilling fluid may contain a total of from about 0.3 wt. % to about 1.0 wt. % rheology modifier, based on the total weight of the oil-based drilling fluid. Thus, when no additional rheology modifiers are present, the oil-based drilling fluid may contain a total of from about 0.2 wt. % to about 0.8 wt. % alkaline-earth diamondoid compound, based on the total weight of the oil-based drilling fluid.

Examples of alkaline-earth diamondoid compounds include magnesium diamondoid compounds, calcium diamondoid compounds, strontium diamondoid compounds, barium diamondoid compounds, and beryllium diamondoid compounds. In some such diamondoid compounds, the diamondoid component may be an adamantane moiety. Thus, further examples of alkaline-earth diamondoid compounds include magnesium adamantane compounds, calcium adamantane compounds, strontium adamantane compounds, barium adamantane compounds, and beryllium adamantane compounds. In illustrative embodiments, the alkaline-earth diamondoid rheology modifier of the oil-based drilling fluid may include a magnesium adamantane compound, calcium adamantane compound, or barium adamantane compound.

The oil-based drilling fluids described thus far according to various embodiments may contain an alkaline-earth diamondoid compound as a rheology modifier. Methods by which the alkaline-earth diamondoid compounds, including magnesium adamantane carboxylate compounds, may be prepared, will now be described together with the structural characteristics of the compounds. It should be understood that the alkaline-earth diamondoid compound of the oil-based drilling fluid is not limited to alkaline-earth diamondoid compounds prepared by the illustrative synthetic techniques. Rather, the alkaline-earth diamondoid compound of the oil-based drilling fluid may be any alkaline-earth diamondoid compound including an alkaline-earth metal and a diamondoid moiety, regardless of how the compound is synthesized.

Illustrative methods for preparing alkaline-earth diamondoid compounds may include mixing an alkaline-earth metal salt and a diamondoid compound having at least one carboxylic acid moiety to form a reactant mixture. In the reactant mixture, the alkaline-earth metal salt may be any alkaline-earth metal compound containing $M^{2+}$ and a counteranion derived from an acid or a base, where $M^{2+}$ is $Mg^{2+}$, $Ca^{2+}$, $Sr^{2+}$, $Ba^{2+}$ or $Be^{2+}$, for example. Non-limiting examples of alkaline-earth metal salts, therefore, include $M(OH)_2$, $MCl_2$, $MBr_2$, $M(NO_3)_2$, and $MSO_4$. In some synthetic routes, the alkaline-earth metal salt may be $M(OH)_2$. Non-limiting examples of magnesium salts, for example, include $Mg(OH)_2$, $MgCl_2$, $MgBr_2$, $Mg(NO_3)_2$, and $MgSO_4$. In some synthetic routes, the alkaline-earth metal salt may be $Mg(OH)_2$.

In the reactant mixture used to prepare the alkaline-earth diamondoid compounds, the diamondoid compound has at least one carboxylic acid moiety. In some embodiments, the at least one carboxylic acid is bonded to any non-bridgehead carbon atom of the diamondoid compound. In some synthetic routes, the diamondoid compound may be chosen from carboxylic acids of adamantane, diamantane, or triamantane. In some synthetic routes, the diamondoid compound may be adamantane 1-carboxylic acid (ACA).

The mixing of the alkaline-earth metal salt and the diamondoid compound may be performed by any suitable method using any suitable apparatus to accomplish intimate mixing. For example, the mixing may be performed using solid-state techniques such as blending or grinding of dry powders. The mixing may be performed with the aid of an aqueous or organic solvent by combining powders and the solvent and subsequently stirring the resultant solution. Optionally, after such a wet mixing procedure, some or all of the solvent may be decanted or filtered from the resultant mixture before the magnesium salt and the diamondoid compound are placed under conditions suitable for their chemical reaction.

The methods for preparing the alkaline-earth metal adamantane salt may further include hydrothermally treating the reactant mixture of the alkaline-earth metal salt and the diamondoid compound at a reaction temperature for a reaction time to form the alkaline-earth metal adamantane carboxylate salt. Hydrothermal treatment generally may include adding an aqueous solvent such as water to the reaction mixture, sealing the reaction mixture in a reaction vessel such as an autoclave, and heating the reaction vessel to the reaction temperature to cause crystallization of the magnesium adamantane carboxylate salt to occur in a high-pressure environment.

The reaction temperature may be chosen to provide sufficient thermodynamic energy for the reaction of the alkaline-earth metal salt and the diamondoid compound to proceed within the reaction vessel while also enabling crystallization of the alkaline-earth metal adamantane carboxylate salt. The reaction temperature should be sufficiently high to enable the reaction to progress but also be sufficiently low to avoid decomposition of the adamantane carboxylate salt or solvation of crystallites. In some synthetic routes, the reaction temperature may be from 100° C. to 200° C., such as 100° C., 110° C., 120° C., 130° C., 140° C., 150° C., 160° C., 170° C., 180° C., 190° C., 200° C., or any other temperature between 100° C. and 200° C. Though in some synthetic routes the reaction temperature may be from 100° C. to 200° C., it is contemplated that other reactions may occur optimally at temperatures lower than 100° C. or higher than 200° C. In other synthetic routes, the reaction temperature may be from 100° C. to 150° C. or from 110° C. to 150° C. In one example, where the alkaline-earth metal salt is $Mg(OH)_2$, the reaction temperature may be 150° C.±10° C.

The reaction time may be chosen to provide sufficient time for crystal growth and development of well-defined morphologies to occur as the alkaline-earth metal adamantane carboxylate salt is formed at the reaction temperature. In some synthetic routes, the reaction time may be longer than 12 h, such as from 12 h to 72 h, from 24 h to 72 h, from 12 h to 48 h, or from 24 h to 48 h, for example. Though in some synthetic routes the reaction time may be longer than 12 h, it is contemplated that when higher reaction temperatures above 150° C. are chosen, for example, the reaction time may be shorter than 12 h.

The methods for preparing the alkaline-earth metal adamantane carboxylate salt may further include customary isolation steps such as cooling or depressurizing the reaction vessel, removing the reaction mixture from the reaction vessel, removing solvent from the reaction mixture by filtering or any other suitable technique, washing the alkaline-earth metal adamantane carboxylate salt with an aqueous or organic solvent that does not dissolve the alkaline-earth metal adamantane carboxylate salt, drying the alkaline-earth metal adamantane carboxylate salt, or any combination of these steps. In some synthetic, the alkaline-earth metal adamantane carboxylate salt may be vacuum filtered from any solvent present in the reaction vessel, washed with water, and dried at a suitable temperature for a suitable time. For example, the alkaline-earth metal adamantane carboxylate salt may be dried at 65° C. for 24 h to drive off residual solvent from the hydrothermal treatment.

In some embodiments of oil-based drilling fluids, the alkaline-earth diamondoid compound may be a magnesium adamantane carboxylate salt prepared as previously described. A magnesium adamantane carboxylate salt prepared using a magnesium salt and ACA will be subsequently described by a shorthand notation Mg(x)-AC, where x is the ratio of $Mg^{2+}$ to ACA in the reaction mixture used to prepare the magnesium adamantane carboxylate salt, and AC represents the carbon support derived from the adamantane moiety of the ACA. For example, Mg(0.5)-AC represents a magnesium adamantane carboxylate salt prepared by reacting $Mg(OH)_2$ and ACA with a 0.5:1 molar ratio of $Mg^{2+}$ to ACA. Likewise, Mg(1.0)-AC represents a magnesium adamantane carboxylate salt prepared by reacting $Mg(OH)_2$ and ACA with a 1.0:1 molar ratio of $Mg^{2+}$ to ACA.

In illustrative methods for preparing a magnesium adamantane salt such as Mg(0.5)-AD, the reaction mixture may be prepared by mixing a magnesium salt such as, for example, $Mg(OH)_2$, and ACA in amounts that provide a ratio of $Mg^{2+}$ to ACA in the reaction mixture of from 0.5:1 to 1.0:1. The specific ratio of $Mg^{2+}$ to ACA in the reaction mixture may be chosen to affect the overall crystal morphology of the magnesium adamantane carboxylate salt to a desired form. Without intent to be bound by theory, it is believed that the crystal morphology of the magnesium adamantane carboxylate salt may be tailored by increasing or decreasing the ratio of $Mg^{2+}$ to ACA in the reaction mixture. Though the ratio of $Mg^{2+}$ to ACA may be selected from 0.5:1 to 1.0:1, it is contemplated that the crystal morphology of the magnesium adamantane carboxylate salt may be further tailored by decreasing the ratio of $Mg^{2+}$ to ACA to below 0.5:1 or by increasing the ratio of $Mg^{2+}$ to ACA to greater than 1.0:1. Even so, a point of saturation is believed to exist, above which additional magnesium ions cannot be incorporated into the magnesium adamantane carboxylate salt.

In general, Mg-AC compounds may exhibit a layered structure or morphology. The layered structure or morphology Mg-AC compounds may manifest as a plurality of layers lacking edge-to-face connections. The plurality of layers may be composed of individual layers each having an aspect ratio greater than 500 or greater than 1000. That is, each of the individual layers may have a length measurement that is at least 500 times or at least 1000 times as long as a thickness measurement of the same layer. For example, the layer may have a length of 10 µm to 20 µm and a thickness of 10 nm to 20 nm. These very thin layers may in turn exhibit exfoliation, particularly in the presence of certain solvents. The Mg-AC material also may form stable dispersions or gels in various solvents such as polar organic solvents. For example, Mg-AC layers may exfoliate in organic solvents such as ethanol and acetone. Without intent to be bound by theory, it is believed that the presence of high-aspect ratio layers that exfoliate in Mg-AC may benefit the overall properties of drilling fluids in which Mg-AC is used as a rheology modifier.

In addition to the oil base continuous phase, the aqueous discontinuous phase, and the rheology modifier including the alkaline-earth metal diamondoid compound, the oil-based drilling fluid may include one or more optional ingredients that tailor the properties of the oil-based drilling fluid to the application for which it is intended. The optional ingredients include, for example, at least one additive chosen from emulsifiers, wetting agents, alkalinity control agents, fluid-loss control agents, suspending agents, weight-adjusting agents, density-adjusting agents, or combinations thereof. In some embodiments, the oil-based drilling fluids may contain at least one emulsifier, at least one wetting agent, at least one alkalinity control agent, at least one fluid-loss control agent, at least one suspending agent, and at least one density adjusting agent.

Optional emulsifiers may be added to the oil-based drilling fluid to facilitate formation of an emulsion and reduce interfacial tension between the base oil continuous phase of the oil-based drilling fluid and the aqueous discontinuous phase of the oil-based drilling fluid. Examples of emulsifiers include surfactants, detergents, lignosulfates, and lignitic compounds.

Optional wetting agents may be added to the oil-based drilling fluid to reduce the tendency of materials such as clay and shale to stick to drilling equipment such as by balling, booting off, or forming mud rings. Examples of wetting agents include surfactants such as anionic surfactants and nonionic surfactants. When wetting agents are used, they may compose from about 0.1 wt. % to about 1.0 wt. % of the oil-based drilling fluid, based on the total weight of the drilling fluid.

Optional fluid-loss control agents may be added to the oil-based drilling fluid to reduce the amount of filtrate lost from the drilling fluid into a subsurface formation. Examples of fluid-loss control agents include organophilic (for example, amine-treated) lignite, bentonite, manufactured polymers, and thinners or deflocculants. When fluid-loss control agents are used, they may compose from about 0.5 wt. % to about 1.5 wt. % of the oil-based drilling fluid, based on the total weight of the drilling fluid.

Optional suspending agents may be added to the oil-based drilling fluid to adjust the viscosity of the drilling fluid to have a yield point at a low shear rate sufficient to suspend all of the drilling fluid components, by which the settling of components of the drilling fluid may be avoided. Examples of suspending agents include fatty acids and fibrous materials. When suspending agents are used, they may compose from about 0.01 wt. % to about 1.0 wt. % of the oil-based drilling fluid, based on the total weight of the drilling fluid.

Optional weight adjusting agents or density adjusting agents may be added to the oil-based drilling fluid to increase the weight, the density, or both, of the oil-based drilling fluid. Weight adjusting agents may be used to control formation pressures and to help combat the effects of sloughing or heaving shales that may be encountered in stressed areas. Any substance that is denser than water and that does not adversely affect other properties of the drilling fluid can be used as a weighting material. Examples of weight adjusting or density adjusting agents include barite ($BaSO_4$), galena (PbS), hematite ($Fe_2O_3$), magnetite ($Fe_3O_4$), manufactured iron oxide, ilmenite ($FeO \cdot TiO_2$), siderite ($FeCO_3$), celesite ($SrSO_4$), dolomite ($CaCO_3 \cdot MgCO_3$), and calcite ($CaCO_3$). When weight or density adjusting agents are used, they may compose from about 65 wt. % to about 75 wt. % of the oil-based drilling fluid, based on the total weight of the drilling fluid.

In some embodiments, therefore, the oil-based drilling fluid may contain from 13 wt. % to 17 wt. % base oil; from 0 wt. % to 1.0 wt. % emulsifier; from 0 wt. % to 0.6 wt. % wetting agent; from 0.3 wt. % to 0.8 wt. % rheology modifier; from 0 wt. % to 1.5 wt. % fluid-loss control additive; from 3.0 wt. % to 5.0 wt. % brine solution; and from 0 wt. % to 75 wt. % weighting additive. The oil-based drilling fluids in general may have a specific gravity of from 0.9 to 2.2.

The oil-based drilling fluid according to any of the various embodiments previously described may be formulated to exhibit physical characteristics that render the oil-based drilling fluids suitable for use under high-pressure high-temperature (HPHT) conditions during drilling operations. The HPHT conditions during drilling operations may involve a wellbore pressure greater than 10,000 psi and a wellbore temperature greater than 300° F. (149° C.). For example, the oil-based drilling fluids including the alkaline-earth metal diamondoid compound rheology modifier may have lower viscosity both before hot rolling and after hot rolling at 100 rpm, compared to a drilling fluid having an identical specific gravity and oil-to-water ratio and identical ingredients in identical proportions to the oil-based drilling fluid but lacking the rheology modifier. Similarly, the oil-based drilling fluids including the alkaline-earth metal diamondoid compound rheology modifier may have a lower after-hot rolling fluid loss at 350° F. (177° C.) and 500 psi, compared to a drilling fluid having an identical specific gravity and oil-to-water ratio and identical ingredients in identical proportions to the oil-based drilling fluid but lacking the rheology modifier. The oil-based drilling fluids including the alkaline-earth metal diamondoid compound rheology modifier may have a higher electrical stability, compared to a drilling fluid having an identical specific gravity and oil-to-water ratio and identical ingredients in identical proportions to the oil-based drilling fluid but lacking the rheology modifier.

Having previously described the oil-based drilling fluids according to various embodiments, illustrative methods for preparing the oil-based drilling fluids will now be described. The methods for preparing the oil-based drilling fluids may include mixing a base oil, optionally at least one emulsifier, and optionally at least one wetting agent using standard mixing techniques to form a first mixture. The ingredients of the first mixture may be added to provide amounts previously described with regard to embodiments of the oil-based drilling fluids. The methods for preparing the oil-based drilling fluids may further include adding and mixing at least one rheology modifier into the first mixture by standard techniques to form a second mixture, wherein the at least one rheology modifier comprises an alkaline-earth diamondoid compound. Again, the ingredients of the second mixture may be added to provide amounts previously described with regard to embodiments of the oil-based drilling fluids. The rheology modifier includes at least one alkaline-earth diamondoid compound such as, for example, a magnesium adamantane carboxylate compound. The at least one alkaline-earth diamondoid compound may be any alkaline-earth diamondoid compound described according to the present specification.

The methods for preparing the oil-based drilling fluids may further include adding and mixing optionally at least one fluid-loss control additive into the second mixture to form a third mixture; adding and mixing a brine solution as a discontinuous phase into the third mixture to form a fourth mixture; and optionally adding and mixing a weighting additive into the fourth mixture to form the oil-based drilling fluid.

The oil-based drilling fluids previously described, including oil-based drilling fluids prepared as previously described or prepared by other industry-acceptable techniques understood by the person of ordinary skill, may be well-suited for use in drilling operations on subterranean formations, particularly for drilling operations performed under HPHT conditions of a wellbore pressure greater than 10,000 psi and a wellbore temperature greater than 300° F. (149° C.). Accordingly, embodiments of methods for drilling in a subterranean formation under high-pressure high-temperature conditions may include providing or using in the drilling of a wellbore into the subterranean formation an oil-based drilling fluid according to any embodiment described in this specification or an oil-based drilling fluid prepared according to any embodiment described in this specification.

In the methods for drilling in a subterranean formation under high-pressure high-temperature conditions, the oil-based drilling fluid including the alkaline-earth metal diamondoid compound rheology modifier, under high-pressure high-temperature conditions, may have a lower viscosity, compared to a drilling fluid having an identical specific gravity and oil-to-water ratio and identical ingredients in identical proportions to the oil-based drilling fluid but lacking the alkaline-earth metal diamondoid compound rheology modifier. Likewise, the oil-based drilling fluid including the alkaline-earth metal diamondoid compound rheology modifier, under high-pressure high-temperature conditions, may have a lower fluid loss, compared to a drilling fluid having an identical specific gravity and oil-to-water ratio and identical ingredients in identical proportions to the oil-based drilling fluid but lacking the alkaline-earth metal diamondoid compound rheology modifier. Likewise, the oil-based drilling fluid including the alkaline-earth metal diamondoid compound rheology modifier, under high-pressure high-temperature conditions, may have a higher electrical stability, compared to a drilling fluid having an identical specific gravity and oil-to-water ratio and identical ingredients in identical proportions to the oil-based drilling fluid but lacking the alkaline-earth metal diamondoid compound rheology modifier.

EXAMPLES

The embodiments described in this specification will be further clarified by the following Examples. It should be understood that the following Examples are not intended to limit the scope of this disclosure or its claims to any particular embodiment.

Example 1

Synthesis and Physical Characterization of Mg(0.5)-Adamantane Carboxylate Salt

Mg-adamantane carboxylate (Mg-AC) compounds were hydrothermally synthesized by mixing $Mg(OH)_2$ and 1-adamantane carboxylic acid (ACA) in amounts to provide a 1:2 molar ratio of $Mg^{2+}$ to ACA to form a reaction mixture, then transferring the reaction mixture to a Teflon-lined stainless-steel autoclave and heating the reaction mixture at 150° C. for 24 h. The reactants were mixed by stirring for 1 h on a magnetic stirrer. The resultant product, Mg(0.5)-AC (where 0.5 refers to the original $Mg^{2+}$-to-ACA mixing ratio and "AC" refers to adamantane carboxylate) was vacuum filtered, washed with a copious amount of water, and then dried at 65° C. for 24 h. Products were characterized by powder X-ray diffraction (PXRD), infra-red (IR) spectroscopy, scanning electron microscopy (SEM), thermogravimetric analysis (TGA), atomic force microscopy (AFM), and transmission electron microscopy (TEM).

The Mg(0.5)-AC was analyzed by PXRD. The PXRD spectrum in FIG. 1 exhibited a series of basal reflections at 2θ angles of 5.7°, 6.6°, 8.0°, 9.2°, and 11.5°, corresponding to d-spacings of 15.41 Å, 13.3 Å, 11.0 Å, 9.6 Å, and 7.7 Å, respectively. Strong reflections occur centered around 2θ angles of 15° to 17°, and several low to medium intensity reflections appeared in the 2θ range 30° to 50°. In addition, low-intensity twin reflections occurred in the 2θ range 57° to 60°. All of these features in the PXRD pattern indicate the formation of a material with a layered structure.

Figure 2:
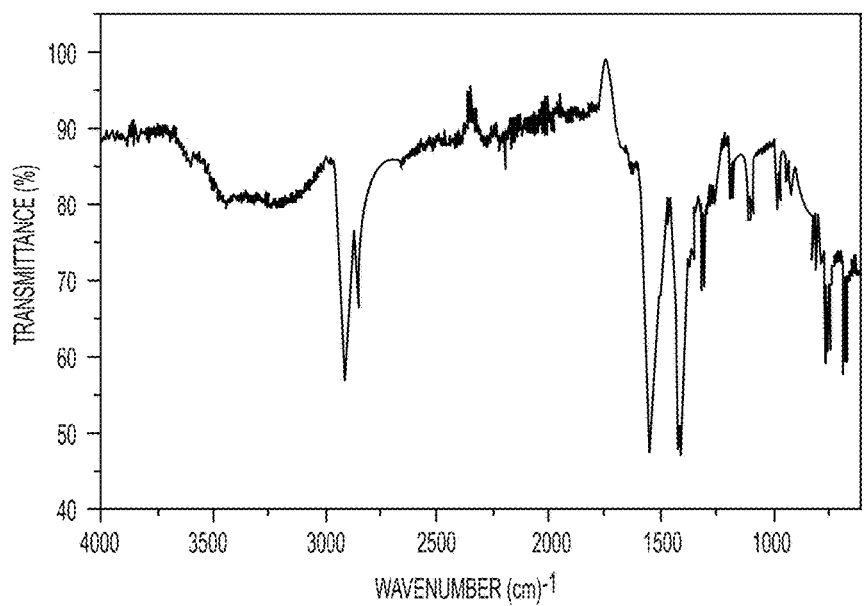
FIG. 2 is an infrared (IR) spectrum of a Mg(0.5)-AC magnesium adamantane carboxylate salt formed from Mg(OH)$_2$ and 1-adamantane carboxylic acid (ACA) with a 0.5:1 molar ratio of Mg$^{2+}$ to ACA.

The Mg(0.5)-AC was further characterized with IR spectroscopy. The IR spectrum in FIG. 2 shows the symmetric and antisymmetric stretching vibrations of the COO$^-$ group at 1411 cm$^{-1}$ and 1550 cm$^{-1}$ respectively. The vibrations at 2900 cm$^{-1}$ and 2847 cm$^{-1}$ arise from the C—H bonds of the adamantane carboxylate ion. The broad vibration in the range of 3200 cm$^{-1}$ to 3400 cm$^{-1}$ arises from the hydrogen-bonded hydroxyl ion. The small shoulder at about 3600 cm$^{-1}$ arises from the non-hydrogen bonded hydroxyl ion and is believed to indicate a small amount of precursor Mg(OH)$_2$ in the resultant product as an impurity. The medium intensity vibrations less than 1000 cm$^{-1}$ arise from the bending and stretching of metal-oxygen bonds.

Figure 3:
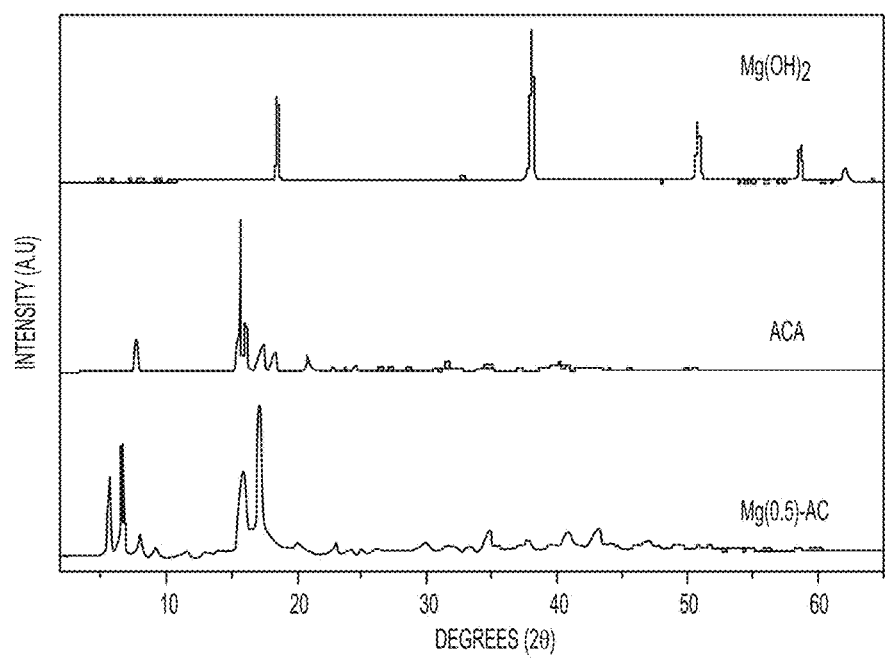
FIG. 3 includes stacked IR spectra of Mg(OH)$_2$, ACA, and Mg(0.5)-AC.

Comparison of starting materials with the Mg(0.5)-AC was undertaken to check the possible impurities and unreacted starting materials. FIG. 3 shows overlaid PXRD patterns of Mg(0.5)-AC, ACA, and Mg(OH)$_2$. The Mg(0.5)-AC has a set of reflections that do not correspond with those of the starting materials, except a low intensity reflection at 37.9° arising from starting Mg(OH)$_2$, which was also confirmed by IR analysis. The twin peaks of ACA (100% intensity) in the 2θ range of 15° to 17° are in the Mg(0.5)-AC as well. The peak positions and full width at half maxima (FWHM) shows that the peaks are shifted in Mg(0.5)-AC more than 1° and are broadened. This precludes the possibility of the starting ACA being present in the Mg(0.5)-AC.

Figure 4:
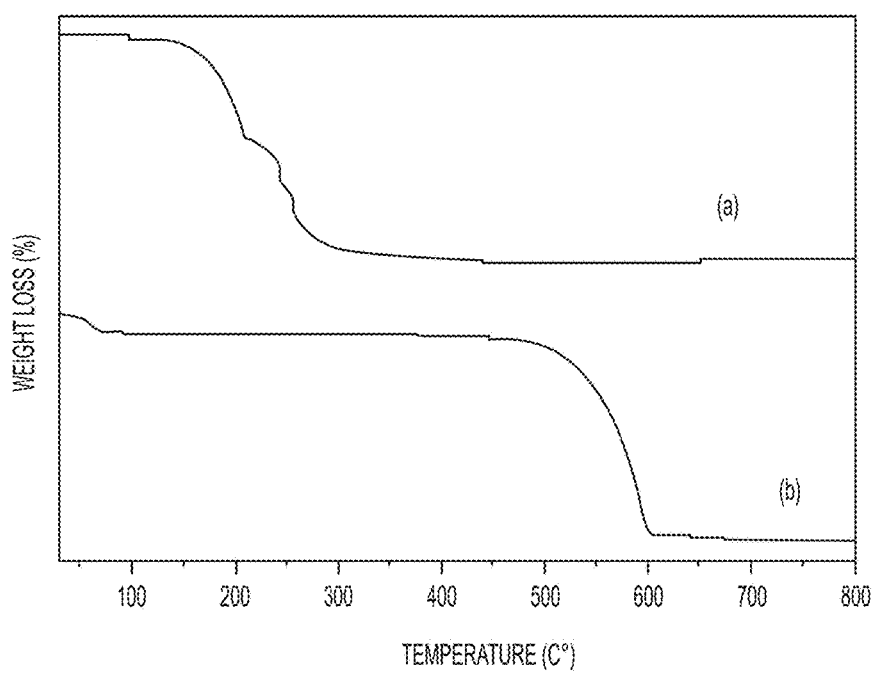
FIG. 4 includes stacked thermogravimetric analyses of (a) ACA; and (b) Mg(0.5)-AC.
Figure 5A:
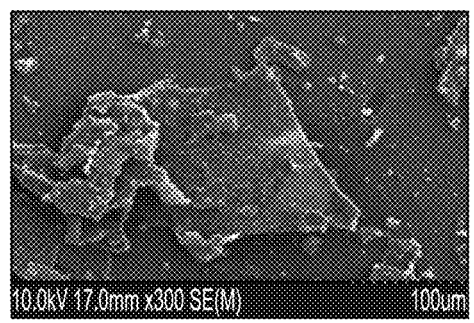
FIGS. 5A-5D are SEM micrographs at various magnifications of Mg(0.5)-AC prepared according to embodiments of this specification.
Figure 5B:
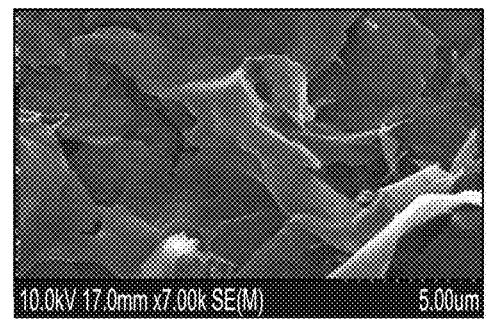
Figure 5C:
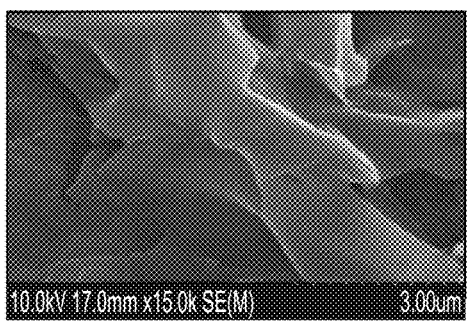
Figure 5D:
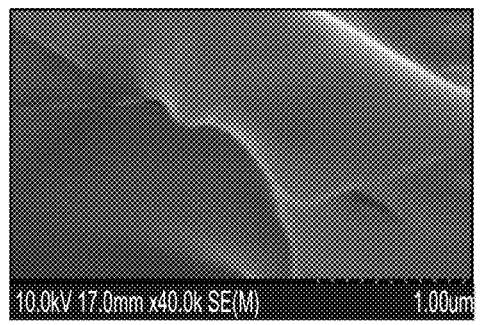

Thermal decomposition behavior of the Mg(0.5)-AC was studied by thermogravimetric analysis (TGA) in a helium gas atmosphere from 30° C. to 800° C. at a heating rate of 10° C./min. The Mg(0.5)-AC shows a two-step mass loss, as shown in plot (b) of FIG. 4. The 5 wt. % to 6 wt. % mass loss around 60° C. may be attributable to adsorbed water. The TGA evidences that the compound is stable up to 450° C. and losses around 85 wt % of its mass in the range of 450° C. to 600° C. The mass loss in this range is attributable to loss of the adamantane carboxylate moiety and hydroxyl ions. The residue is only around 10 wt. %, indicating the formation of highly porous nanoscale MgO. The single step mass loss, except the loss of adsorbed water confirms the single-phase nature of the Mg(0.5)-AC. In contrast and as illustrated in plot (a) of FIG. 4, the starting ACA shows entirely different thermal behavior. Adamantane carboxylic acid was found to be stable up to 100° C. and to decompose completely in a single step between 120° C. and 300° C. Without intent to be bound by theory, it is believed that the unusually high thermal stability of the Mg(0.5)-AC may arise from the formation of Mg$^{2+}$-adamantane carboxylate ion bonding.

The morphology and nature of the Mg(0.5)-AC was further characterized by SEM. The SEM images of Mg(0.5)-AC in FIGS. 5A-5D at various magnifications evidence a layered morphology. The layers have very large aspect ratios, with dimensions of several microns in length and thickness of several nanometers. The layers are stacked one above the other and do not appear to have edge-to-face sharing connections that are common for many types of layered solids have. The absence of edge-to-face sharing connections in the Mg(0.5)-AC may indicate that the Mg(0.5)-AC can be easily exfoliated.

Example 2

Dispersion and Exfoliation of Mg(0.5)-Adamantane Carboxylate Salt

Based on its physical characterizations, the Mg(0.5)-AC has been found to be a layered structure with high aspect ratio and high thermal stability. Therefore, the Mg(0.5)-AC is believed to have qualities well suited for using the Mg(0.5)-AC as a rheology modifier for drilling fluids. To check the suitability of Mg(0.5)-AC to blend with various polymers and ability to form dispersions, various polar and nonpolar solvents were used. The dispersion studies were carried out by using six different solvents with a variety of physical properties. Dispersion studies of the product in various solvents were carried out on 100 mg of Mg(0.5)-AC in 100 mL of various solvents to form a suspension that was stirred for 24 h on a magnetic stirrer. The results of the study are provided in TABLE 1.

TABLE 1

| Solvent | Solvent Type | Dispersion Characteristic |
| --- | --- | --- |
| Water | Polar | No dispersion |
| Ethanol | Polar | Stable dispersion |
| Tetrahydrofuran | Polar | Stable dispersion |
| N,N-Dimethylformamide | Polar | Stable gel |
| 1,4-Dioxane | Polar | Stable dispersion |
| Pentane | Nonpolar | No dispersion |

The Mg(0.5)-AC did not show any exfoliation or any kind of dispersion with water, indicating the hydrophobic nature of the compound. When a polar organic solvent such as ethanol was used, the Mg(0.5)-AC formed a dispersion within 30 min. The Mg(0.5)-AC dispersed in 1,4-dioxane and formed a stable gel with N,N-dimethyl formamide. The Mg(0.5)-AC was found to form a stable dispersion with widely used tetrahydrofuran (THF). This shows that Mg(0.5)-AC has the ability to form stable dispersions with polar organic solvents and can be used as a filler in various nanocomposites involving organic polymers. On the other hand, the Mg(0.5)-AC did not show any exfoliation with nonpolar pentane.

Figures 6A, 6B:
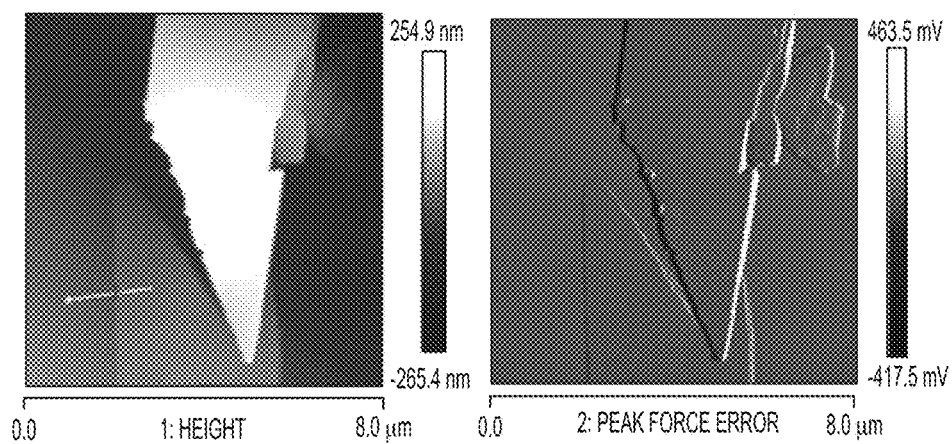
FIG. 6A is an atomic-force micrograph of a selected area of an exfoliated Mg(0.5)-AC particle removed from a colloidal suspension.
FIG. 6B is a representation of the peak force errors in the micrograph of FIG. 6A.
Figure 6C:
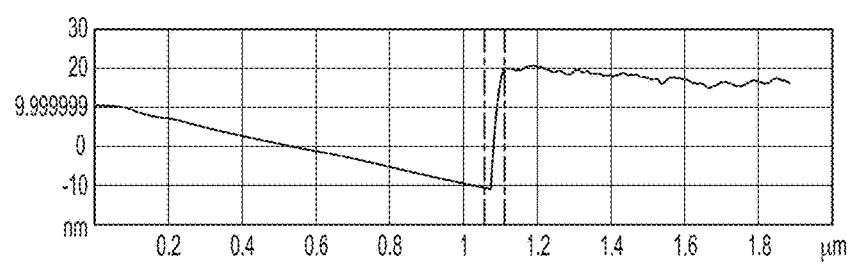
FIG. 6C is a graph of height profile in the exfoliated particle, measured across the path indicated in FIG. 6A.

The exfoliated Mg(0.5)-AC colloidal suspensions were characterized by AFM to see the extent of exfoliation. FIG. 6A shows the topological profile of a selected area of an exfoliated Mg(0.5)-AC particle removed from a colloidal ethanol suspension of Mg-AC particles. FIG. 6B shows the peak-force errors in the same measurement. FIG. 6C is a height profile of the particle, measured along the path indicated in FIG. 6A. The exfoliated samples show the layers having thickness of 10 nm to 20 nm and a lateral dimension greater than 10 µm. These dimensions are equivalent to an aspect ratio of from 500 to 1000.

Example 3

Effect of Mg Supersaturation on Phase Formation and Morphology

The supersaturation of the initial reaction mixture plays a crucial role in phase formation of any material. The Mg(0.5)-AC prepared in Example 1 had a Mg$^{2+}$/ACA ratio of 1:2. To characterize the effect of Mg$^{2+}$/ACA ratio on the Mg-adamantane phase formation, Mg(1.0)-AC was prepared by the same synthetic route as described in Example 1, except that the initial reactants were mixed to provide a Mg$^{2+}$/ACA ratio of 1:1. Thus, the Mg(1.0)-AC was prepared with a larger molar fraction of Mg$^{2+}$ compared to the Mg(0.5)-AC of Example 1.

Figure 7:
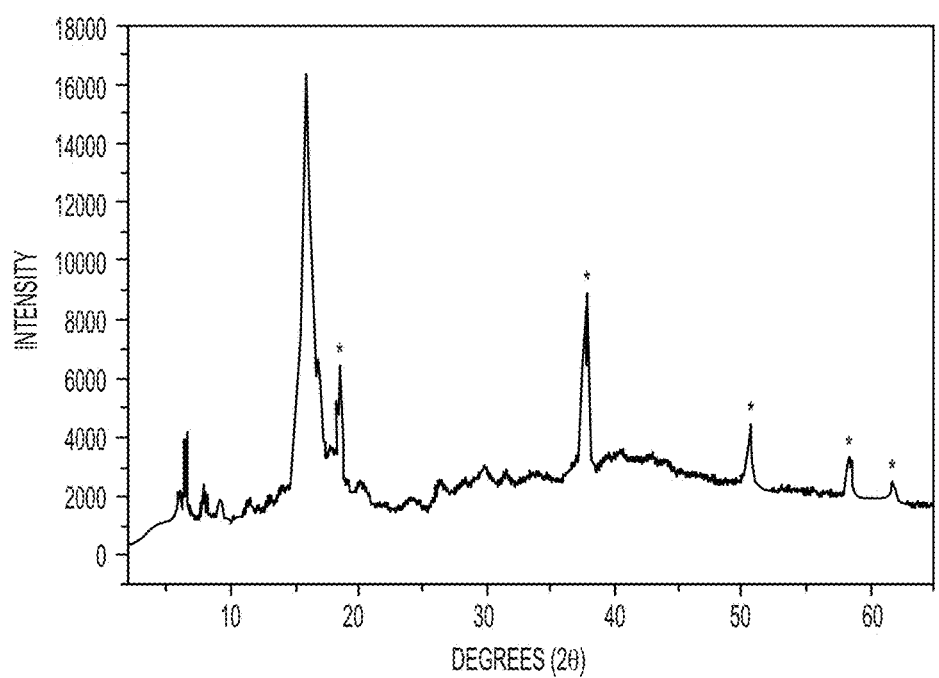
FIG. 7 is PXRD pattern of a Mg(1.0)-AC magnesium adamantane salt formed from Mg(OH)$_2$ and 1-adamantane carboxylic acid (ACA) with a 1.0:1 molar ratio of Mg$^{2+}$ to ACA.
Figure 8A:
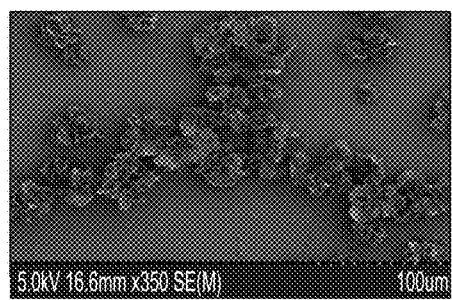
FIGS. 8A-8D are SEM micrographs at various magnifications of Mg(1.0)-AC nanocomposite prepared according to embodiments of this specification.
Figure 8B:
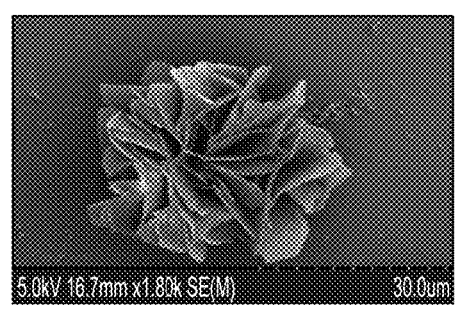
Figure 8C:
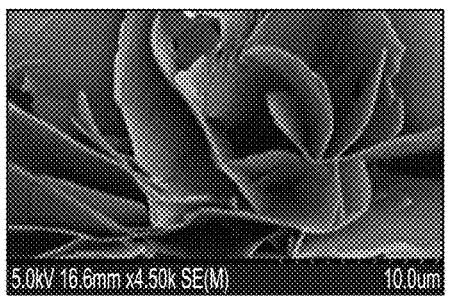
Figure 8D:
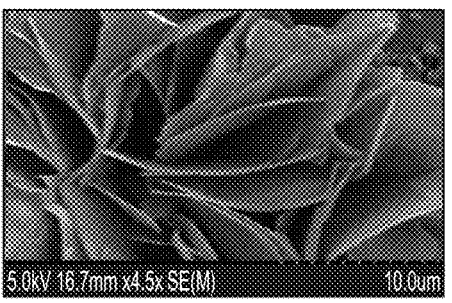

The PXRD pattern of the Mg(1.0)-AC in FIG. 7 retains all the reflections corresponding to Mg-AC, as compared to the PXRD of Mg(0.5)-AC (FIG. 1). In addition, the Mg(1.0)-AC PXRD spectrum shows several high intensity reflections (marked with *) believed to arise from unreacted Mg(OH)$_2$. The appearance of unreacted starting material in the Mg(1.0)-AC illustrates that stoichiometric ratio of the starting materials Mg(OH)$_2$ and ACA affects whether or not the resulting Mg-AC material will be a single phase material.

The Mg(1.0)-AC was further characterized with SEM to ascertain the effect of Mg$^{2+}$/ACA on the morphology of the material. FIGS. 8A-8D are SEM images of Mg(1.0)-AC at various magnifications. The morphology of Mg(1.0)-AC appears to be different from that of Mg(0.5)-AC. Though the SEM of Mg(1.0)-AC shows the layered morphology with large layers as with Mg(0.5)-AC, the crystallites of Mg(1.0)-AC appear to be connected through edge-to-face sharing, giving rise to a sand-flower morphology. Thus, by changing the concentration of Mg$^{2+}$ and ACA in the starting reaction mixture, it is possible to provide Mg-AC with a different morphology and orientation. In addition to the Mg-AC phase, the SEM of Mg(1.0)-AC also shows aggregated, featureless particles of unreacted Mg(OH)$_2$.

Example 4

Drilling Fluid Formulation and Characterizations

To compare the physical and rheological properties of a drilling fluid containing a magnesium adamantane compound with those of a drilling fluid containing a clay modifier, two drilling fluids were prepared. The two drilling fluids were based on the M-I SWACO RHADIANT™ system that includes a blend of three proprietary emulsifiers and fluid-loss control agents specially tailored for oil-based fluid formulations. An ideal drilling fluid was prepared as a basis for comparison, using BENTONE® 42 as a rheology modifier. BENTONE® 42 is a hectorite organoclay optimized for synthetic base oil systems and is available from Elementis Specialties. A second drilling fluid was prepared by replacing the BENTONE® 42 in the comparative drilling fluid with an equal weight of Mg(0.5)-AC, prepared according to Example 1, as the rheology modifier.

The two drilling fluids were formulated using the following ingredients: Saraline 185V, a synthetic oil drilling base fluid, available from Shell (Houston, Tex.); SUREMUL®, an amidoamine surfactant, available from M-I SWACO, LLC (Houston, Tex.); SUREWET®, a wetting agent, available from M-I SWACO, LLC (Houston, Tex.); MUL XT, an emulsifier for use in non-aqueous fluid systems, available from M-I SWACO, LLC (Houston, Tex.); VERSAGEL HT, a hectorite clay viscosifier for aiding in filtercake formation and filtration control, available from M-I SWACO, LLC (Houston, Tex.); ONE-TROL™ HT, an amine-treated tannin filtration control additive designed for use in oil and synthetic-base drilling fluid systems, available from M-I SWACO, LLC (Houston, Tex.); ECOTROL RD, a filtration control additive designed for use in oil and synthetic-base drilling fluid systems, available from M-I SWACO, LLC (Houston, Tex.); and M-I BAR, a barite (BaSO$_4$) weighting agent, available from M-I SWACO, LLC (Houston, Tex.).

Both drilling fluids were prepared in 772 g (351 mL) quantities using a Hamilton Beach Mixer. The formulations for both drilling fluids are provided in TABLE 2. To prepare the drilling fluids, the base oil, emulsifiers, and wetting agents were mixed together first for 5 minutes during stage 1, and then the viscosity modifiers and rheology modifiers were added and mixed for another 10 minutes during stage 2. Next, in stage 3 the fluid-loss control additives were added and mixed for 10 minutes, followed by brine in stage 4 and barite in stage 5, which were mixed for 15 minutes and 20 minutes, respectively. The quantity of base oil used and barite were slightly different for the Mg(0.5)-AC formulation to provide a specific gravity of 2.20 and an oil/water ratio of 90.0, identical to the respective properties of comparative drilling fluid.

TABLE 2

| Ingredient | Function | Model Fluid (Comparative) | Fluid with Mg(0.5)-AC | Mixing Order and Time |
|---|---|---|---|---|
| Saraline 185V | Base Oil | 122.0 g (157.01 ml) | 120.9 g (155.60 ml) | Stage 1 |
| SUREMUL | Emulsifier | 10.0 g (10.42 ml) | 10.0 g (10.42 ml) | (5 min) |
| SUREWET | Wetting Agent | 4.0 g (4.17 ml) | 4.0 g (4.17 ml) | |
| MUL XT | Emulsifier | 4.0 g (4.21 ml) | 4.0 g (4.21 ml) | |
| VERSAGEL HT | Viscosifier | 2.75 g (1.62 ml) | 2.75 g (1.62 ml) | Stage 2 |
| BENTONE 42 | Rheology Modifier | 2.75 g (1.62 ml) | 0 | (10 min) |
| Mg(0.5)-AD | Rheology Modifier | 0 | 2.75 g (1.62 ml) | |
| Lime | Alkalinity Control | 6.0 g (2.56 ml) | 6.0 g (2.56 ml) | |
| ONE-TROL HT | Fluid Loss Control | 8.0 g (6.20 ml) | 8.0 g (6.20 ml) | Stage 3 |
| ECOTROL RD | Fluid Loss Control | 0.8 g (0.44 ml) | 0.8 g (0.44 ml) | (10 min) |
| CaCl$_2$ brine | Internal Phase | 28.5 g (20.96 ml) | 28.5 g (20.96 ml) | Stage 4 |
| Fresh water | Internal Phase | 5.9 g 5.90 ml) | 5.9 g (5.90 ml) | (15 min) |
| M-I BAR | Weight Material | 577.2 g (135.49 ml) | 577.3 g (135.52 ml) | Stage 5 (20 min) |
| | Total | 771.90 g (350.60 ml) | 770.90 g (349.21 ml) | 60 min |
| | Specific Gravity | 2.202 | 2.208 | |
| | Oil/Water Ratio (volumetric) | 90.103 | 90.030 | |

The viscosities of the OBMs were tested using a Fann 35 viscometer. The drilling fluids were placed in Fann 35 heating cups after their preparations and were stirred 600 revolutions per minute (rpm) until the fluids reached temperatures of 120° F. (49° C.). The viscosities were measured at the shear rates of 600 rpm, 300 rpm, 200 rpm, 100 rpm, 6 rpm, and 3 rpm, both before hot rolling (BHR) and after hot rolling (AHR). The hot rolling was performed at 350° F. (177° C.) and 150 psi for 16 hours in aging cells. The gel strengths of the drilling fluids BHR and AHR were measured by taking two readings after the drilling fluids in the cup were stirred each time at 600 rpm and then rested for (1) 10 seconds and (2) 10 minutes, respectively.

The fluid loss (FL) test on each drilling fluid was carried out on hot-rolled drilling fluids by using a filtration apparatus (API filter press OFITE® apparatus) by placing each drilling fluid into stainless steel chambers having an opening at the bottom. A filter paper was placed on the bottom of the chamber, and the drilling fluid was exposed to a pressure of 500 psi at 350° F. (177° C.) for 30 minutes. No water was present in the collected fluids from both comparative drilling fluid mud and the drilling fluid containing Mg(0.5)-AC. The electrical stabilities (ES) of both fluids were measured both BHR and AHR using an Electrical Stability Meter.

Results from the viscosity testing, the fluid loss testing, and the electrical stability testing are provided in TABLE 3.

TABLE 3

| Fluid properties at 120° F. | Model Fluid (Comparative) | | Fluid with Mg(0.5)-AC | |
|---|---|---|---|---|
| | BHR | AHR | BHR | AHR |
| 600 rpm | 152 | 149 | 149 | 125 |
| 300 rpm | 86 | 80 | 76 | 68 |
| 200 rpm | 62 | 55 | 53 | 47 |
| 100 rpm | 37 | 32 | 31 | 27 |
| 6 rpm | 9 | 6 | 7 | 6 |
| 3 rpm | 7 | 5 | 6 | 5 |
| 10 s gel | 7 | 7 | 6 | 7 |
| 10 min gel | 8 | 7 | 6 | 9 |
| PV (cP) | 66 | 69 | 73 | 57 |
| YP (lbf/100 ft$^2$) | 20 | 11 | 3 | 11 |
| ES (V) | 1173 | 402 | 1559 | 1022 |
| 2 × HPHT FL (mL) at 350° F. | — | 6.8 | — | 4.2 |

The drilling fluid containing the magnesium adamantane as a viscosity modifier showed promising results as a HPHT drilling fluid, owing to its lower viscosity both BHR and AHR at 100 rpm than that of the comparative drilling fluid containing the BENTONE 42 as the rheology modifier. The viscosity values at 100 rpm reflect the viscosities in the drilling fluid within the annulus of the wellbore. Therefore, lower numbers indicate a higher performance of drilling fluid. The rheology of the Mg-AD drilling fluid was similar to that of the comparative drilling fluid at 6 rpm after hot rolling, showing less thermal breakdown in the Mg-AD fluid than in the comparative fluid. The AHR fluid loss (FL) at 350° F. (177° C.) and 500 psi, for the Mg-AC containing fluid was less than that of the AHR comparative fluid. The AHR electrical stability (ES) of the Mg-AC drilling fluid was also greater than that of the comparative fluid, indicating better emulsion stability of the Mg-AC drilling fluid that was retained after hot rolling. Unlike the plastic viscosity of the comparative fluid, the plastic viscosity of Mg-AC drilling fluid decreased AHR and did not become viscous at high temperatures. The plastic viscosity of the Mg-AC drilling fluid decreasing maintains the ability to drill without extra power required during drilling operations. Conversely, a higher PV after exposure to high temperature, as in the comparative fluid, would mean extra power required to circulate the viscous fluid.

Thus, the rheology data from the two drilling fluids indicates that substitution of the BENTONE 42 in the comparative fluid with an equal amount of Mg(0.5)-AC resulted in a drilling fluid formulation having not only acceptable performance characteristics but also improved characteristics. The magnesium adamantane carboxylate compounds, therefore, are believed to be highly suitable rheology modifiers for use in drilling fluids that can, among other things, suspend drill cuttings in a static condition during HPHT drilling operations.

It should now be understood the various aspects of the oil-based drilling fluid, the method of preparing the same, and the method of drilling in a subterranean formation under high-pressure high-temperature conditions utilizing the same are described and such aspects may be utilized in conjunction with various other aspects.

In a first aspect, the disclosure provides an oil-based drilling fluid. The oil-based drilling fluid comprises a base oil continuous phase, an aqueous discontinuous phase, and at least one rheology modifier. The at least one rheology modifier comprises an alkaline-earth diamondoid compound.

In a second aspect, the disclosure provides the oil-based drilling fluid of the first aspect, in which the alkaline-earth diamondoid compound is chosen from a magnesium diamondoid compound, a calcium diamondoid compound, a strontium diamondoid compound, a barium diamondoid compound, or a beryllium diamondoid compound.

In a third aspect, the disclosure provides the oil-based drilling fluid of the first aspect, in which the alkaline-earth diamondoid compound is chosen from a magnesium adamantane compound, a calcium adamantane compound, a strontium adamantane compound, a barium adamantane compound, or a beryllium adamantane compound.

In a fourth aspect, the disclosure provides the oil-based drilling fluid of the first aspect, in which the alkaline-earth diamondoid compound is a magnesium adamantane carboxylate compound.

In a fifth aspect, the disclosure provides the oil-based drilling fluid of the first aspect, in which the alkaline-earth diamondoid compound is a magnesium adamantane carboxylate compound prepared by mixing a magnesium salt and a diamondoid compound having at least one carboxylic acid moiety to form a reactant mixture and hydrothermally treating the reactant mixture at a reaction temperature for a reaction time to form the magnesium adamantane carboxylate salt In a sixth aspect, the disclosure provides the oil-based drilling fluid of the fifth aspect, in which the magnesium salt and the diamondoid compound are mixed in amounts that provide a ratio of $Mg^{2+}$ to diamondoid compound in the reaction mixture of from 0.5:1 to 1.0:1.

In a seventh aspect, the disclosure provides the oil-based drilling fluid of the fifth or sixth aspects, in which the magnesium salt is $Mg(OH)_2$.

In an eighth aspect, the disclosure provides the oil-based drilling fluid of any of the fifth through seventh aspects, in which the diamondoid compound is 1-adamantane carboxylic acid.

In a ninth aspect, the disclosure provides the oil-based drilling fluid of any of the fifth through eighth aspects, in which the reaction temperature is from 100° C. to 180° C.

In a tenth aspect, the disclosure provides the oil-based drilling fluid of any of the fifth through ninth aspects, in which the reaction temperature is from 140° C. to 160° C.

In an eleventh aspect, the disclosure provides the oil-based drilling fluid of any of the fifth through tenth aspects, in which the reaction time is at least 12 hours.

In a twelfth aspect, the disclosure provides the oil-based drilling fluid of any of the fifth through eleventh aspects, in which the magnesium adamantane carboxylate salt comprises a layered morphology.

In a thirteenth aspect, the disclosure provides the oil-based drilling fluid of the twelfth aspect, in which the layered morphology comprises a plurality of layers lacking edge-to-face connections.

In a fourteenth aspect, the disclosure provides the oil-based drilling fluid of the twelfth or thirteenth aspects, in which the layered morphology comprises a plurality of layers each having aspect ratios greater than 500.

In a fifteenth aspect, the disclosure provides the oil-based drilling fluid of any of the first through fourteenth aspects, in which the base oil continuous phase comprises a base oil chosen from a synthetic oil comprising an ester or olefin, a diesel oil, or a mineral oil, wherein the synthetic oil, the diesel oil, or the mineral oil comprises hydrocarbons chosen from n-paraffins, iso-paraffins, cyclic alkanes, branched alkanes, or mixtures thereof.

In a sixteenth aspect, the disclosure provides the oil-based drilling fluid of any of the first through fifteenth aspects, in which the oil-based drilling fluid has an oil-to-water ratio by volume of from 50:50 to 95:5.

In a seventeenth aspect, the disclosure provides the oil-based drilling fluid of any of the first through sixteenth aspects, in which the oil-based drilling fluid further comprises at least one additive chosen from emulsifiers, wetting agents, alkalinity control agents, fluid-loss control agents, suspending agents, weight-adjusting agents, density-adjusting agents, or combinations thereof.

In an eighteenth aspect, the disclosure provides the oil-based drilling fluid of any of the first through sixteenth aspects, in which the oil-based drilling fluid further comprises at least one emulsifier, at least one wetting agent, at least one alkalinity control agent, at least one fluid-loss control agent, at least one suspending agent, and at least one density adjusting agent.

In a nineteenth aspect, the disclosure provides the oil-based drilling fluid of any of the first through eighteenth aspects, in which the aqueous discontinuous phase contains a brine chosen from calcium chloride, calcium bromide, sodium chloride, sodium bromide, and combinations thereof.

In a twentieth aspect, the disclosure provides the oil-based drilling fluid of any of the first through nineteenth aspects, in which the oil-based drilling fluid comprises from 0.1 wt. % to 1.0 wt. % rheology modifier, based on the total weight of the oil-based drilling fluid.

In a twenty-first aspect, the disclosure provides the oil-based drilling fluid of any of the first through twentieth aspects, in which the oil-based drilling fluid comprises, based on the total weight of the oil-based drilling fluid:
    from 10 wt. % to 17 wt. % base oil;
    from 0.5 wt. % to 2.0 wt. % emulsifier;
    from 0.2 wt. % to 0.6 wt. % wetting agent;
    from 0.2 wt. % to 1.0 wt. % rheology modifier;
    from 0.5 wt. % to 1.5 wt. % fluid-loss control additive;
    from 2.5 wt. % to 5.0 wt. % brine solution; and
    from 65.0 wt. % to 78.0 wt. % weighting additive.

In a twenty-second aspect, the disclosure provides the oil-based drilling fluid of any of the first through twenty-first aspects, in which the oil-based drilling fluid exhibits physical characteristics suitable for use of the oil-based drilling fluid under high-pressure high-temperature conditions during drilling operations.

In a twenty-third aspect, the disclosure provides the oil-based drilling fluid of any of the first through twenty-second aspects, in which high-pressure high-temperature conditions during drilling operations comprise a wellbore pressure greater than 10,000 psi and a wellbore temperature greater than 300° F.

In a twenty-fourth aspect, the disclosure provides the oil-based drilling fluid of any of the first through twenty-third aspects, in which the oil-based drilling fluid with the rheology modifier has lower viscosity both before hot rolling and after hot rolling at 100 rpm, compared to a drilling fluid having an identical specific gravity and oil-to-water ratio and identical ingredients in identical proportions to the oil-based drilling fluid but lacking the rheology modifier.

In a twenty-fifth aspect, the disclosure provides the oil-based drilling fluid of any of the first through twenty-fourth aspects, in which the oil-based drilling fluid with the rheology modifier has a lower after-hot rolling fluid loss at 350° F. (177° C.) and 500 psi, compared to a drilling fluid having an identical specific gravity and oil-to-water ratio and identical ingredients in identical proportions to the oil-based drilling fluid but lacking the rheology modifier.

In a twenty-sixth aspect, the disclosure provides the oil-based drilling fluid of any of the first through twenty-fifth aspects, in which the oil-based drilling fluid with the rheology modifier has higher electrical stability, compared to a drilling fluid having an identical specific gravity and oil-to-water ratio and identical ingredients in identical proportions to the oil-based drilling fluid but lacking the rheology modifier.

In a twenty-seventh aspect, the disclosure provides a method for preparing an oil-based drilling fluid. The method comprises mixing a base oil, at least one emulsifier, and at least one wetting agent to form a first mixture, adding and mixing at least one rheology modifier into the first mixture to form a second mixture, where the at least one rheology modifier comprises an alkaline-earth diamondoid compound, adding and mixing at least one fluid-loss control additive into the second mixture to form a third mixture, adding and mixing a brine solution into the third mixture to form a fourth mixture, and adding and mixing a weighting additive into the fourth mixture to form the oil-based drilling fluid.

In a twenty-eighth aspect, the disclosure provides the method of the twenty-seventh aspect, in which the alkaline-earth diamondoid compound is chosen from a magnesium diamondoid compound, a calcium diamondoid compound, a strontium diamondoid compound, a barium diamondoid compound, or a beryllium diamondoid compound.

In a twenty-ninth aspect, the disclosure provides the method of the twenty-seventh aspect, in which the alkaline-earth diamondoid compound is chosen from a magnesium adamantane compound, a calcium adamantane compound, a strontium adamantane compound, a barium adamantane compound, or a beryllium adamantane compound.

In a thirtieth aspect, the disclosure provides the method of the twenty-seventh aspect, in which the alkaline-earth diamondoid compound is a magnesium adamantane compound.

In a thirty-first aspect, the disclosure provides the method of the twenty-seventh aspect, in which the alkaline-earth diamondoid compound is a magnesium adamantane carboxylate compound prepared by mixing a magnesium salt and a diamondoid compound having at least one carboxylic acid moiety to form a reactant mixture and hydrothermally treating the reactant mixture at a reaction temperature for a reaction time to form the magnesium adamantane carboxylate salt.

In a thirty-second aspect, the disclosure provides the method of the thirty-first aspect, in which the magnesium salt and the diamondoid compound are mixed in amounts that provide a ratio of $Mg^{2+}$ to diamondoid compound in the reaction mixture of from 0.5:1 to 1.0:1.

In a thirty-third aspect, the disclosure provides the method of the thirty-first or thirty-second aspect, in which the magnesium salt is $Mg(OH)_2$.

In a thirty-fourth aspect, the disclosure provides the method of any of the thirty-first through thirty-third aspects, in which the diamondoid compound is 1-adamantane carboxylic acid.

In a thirty-fifth aspect, the disclosure provides the method of any of the thirty-first through thirty-fourth aspects, in which the reaction temperature is from 100° C. to 180° C.

In a thirty-sixth aspect, the disclosure provides the method of any of the thirty-first through thirty-fifth aspects, in which the reaction temperature is from 140° C. to 160° C.

In a thirty-seventh aspect, the disclosure provides the method of any of the thirty-first through thirty-sixth aspects, in which the reaction time is at least 12 hours.

In a thirty-eighth aspect, the disclosure provides the method of any of the thirty-first through thirty-seventh aspects, in which the magnesium adamantane carboxylate salt comprises a layered morphology.

In a thirty-ninth aspect, the disclosure provides the method of the thirty-eighth, in which the layered morphology comprises a plurality of layers lacking edge-to-face connections.

In a fortieth aspect, the disclosure provides the method of the thirty-eighth or thirty-ninth aspect, in which the layered morphology comprises a plurality of layers each having aspect ratios greater than 500.

In a forty-first aspect, the disclosure provides the method of any of the twenty-seventh through fortieth aspects, in which the base oil continuous phase comprises a base oil chosen from a synthetic oil comprising an ester or olefin, a diesel oil, or a mineral oil, wherein the synthetic oil, the diesel oil, or the mineral oil comprises hydrocarbons chosen from n-paraffins, iso-paraffins, cyclic alkanes, branched alkanes, or mixtures thereof.

In a forty-second aspect, the disclosure provides the method of any of the twenty-seventh through forty-first aspects, in which the oil-based drilling fluid has an oil-to-water ratio by volume of from 50:50 to 95:5.

In a forty-third aspect, the disclosure provides the method of any of the twenty-seventh through forty-second aspects, in which the oil-based drilling fluid comprises from 0.1 wt. % to 1.0 wt. % rheology modifier, based on the total weight of the oil-based drilling fluid.

In a forty-fourth aspect, the disclosure provides the method of any of the twenty-seventh through forty-third aspects, in which the brine solution is chosen from calcium chloride, calcium bromide, sodium chloride, sodium bromide, and combinations thereof.

In a forty-fifth aspect, the disclosure provides the method of any of the twenty-seventh through forty-fourth aspects, in which the oil-based drilling fluid comprises, based on the total weight of the oil-based drilling fluid:
from 13 wt. % to 17 wt. % base oil;
from 0.2 wt. % to 2.0 wt. % emulsifier;
from 0.1 wt. % to 1.0 wt. % wetting agent;
from 0.2 wt. % to 1.0 wt. % rheology modifier;
from 0.5 wt. % to 1.5 wt. % fluid-loss control additive;
from 2.0 wt. % to 6.0 wt. % brine solution; and from 65 wt. % to 78 wt. % weighting additive.

In a forty-sixth aspect, the disclosure provides a method for drilling in a subterranean formation under high-pressure high-temperature conditions. The method comprises providing or using in the drilling of a wellbore into the subterranean formation an oil-based drilling fluid according to any one of the first through twenty-sixth or an oil-based drilling fluid prepared according to the method of any one of the twenty-seventh through forty-fifth aspects.

It will be apparent to those skilled in the art that various modifications and variations can be made to the embodiments described herein without departing from the spirit and scope of the claimed subject matter. Thus it is intended that the specification cover the modifications and variations of the various embodiments described herein provided such modification and variations come within the scope of the appended claims and their equivalents.

What is claimed is:

1. An oil-based drilling fluid comprising:
   a base oil continuous phase;
   an aqueous discontinuous phase; and
   at least one rheology modifier, the at least one rheology modifier comprising a magnesium adamantane carboxylate compound.

2. The oil-based drilling fluid of claim 1, where the alkaline-earth diamondoid compound is a magnesium adamantane carboxylate compound prepared by:
   mixing a magnesium salt and a diamondoid compound having at least one carboxylic acid moiety to form a reactant mixture; and
   hydrothermally treating the reactant mixture at a reaction temperature for a reaction time to form the magnesium adamantane carboxylate salt.

3. The oil-based drilling fluid of claim 2, where the magnesium salt and the diamondoid compound are mixed in amounts that provide a ratio of $Mg^{2+}$ to diamondoid compound in the reaction mixture of from 0.5:1 to 1.0:1.

4. The oil-based drilling fluid of claim 2, where the diamondoid compound is 1-adamantane carboxylic acid.

5. The oil-based drilling fluid of claim 2, where the magnesium adamantane carboxylate salt comprises a layered morphology.

6. The oil-based drilling fluid of claim 1, where the oil-based drilling fluid comprises from 0.1 wt.% to 1.0 wt.% rheology modifier, based on the total weight of the oil-based drilling fluid.

7. The oil-based drilling fluid of claim 1, where the oil-based drilling fluid exhibits physical characteristics suitable for use of the oil-based drilling fluid under high-pressure high-temperature conditions during drilling operations, where high-pressure high-temperature conditions during drilling operations comprise a wellbore pressure greater than 10,000 psi and a wellbore temperature greater than 300° F.

8. The oil-based drilling fluid of claim 1, where the oil-based drilling fluid with the rheology modifier has lower viscosity both before hot rolling and after hot rolling at 100 rpm, compared to a drilling fluid having an identical specific gravity and oil-to-water ratio and identical ingredients in identical proportions to the oil-based drilling fluid but lacking the rheology modifier.

9. The oil-based drilling fluid of claim 1, where the oil-based drilling fluid with the rheology modifier has a lower after-hot rolling fluid loss at 350° F. (177° C.) and 500 psi, compared to a drilling fluid having an identical specific gravity and oil-to-water ratio and identical ingredients in identical proportions to the oil-based drilling fluid but lacking the rheology modifier.

10. The oil-based drilling fluid of claim 1, where the oil-based drilling fluid with the rheology modifier has higher electrical stability, compared to a drilling fluid having an identical specific gravity and oil-to-water ratio and identical ingredients in identical proportions to the oil-based drilling fluid but lacking the rheology modifier.

11. A method for preparing an oil-based drilling fluid, the method comprising:
    mixing a base oil, at least one emulsifier, and at least one wetting agent to form a first mixture;
    adding and mixing at least one rheology modifier into the first mixture to form a second mixture, wherein the at least one rheology modifier comprises a magnesium adamantane carboxylate compound;

adding and mixing at least one fluid-loss control additive into the second mixture to form a third mixture;

adding and mixing a brine solution into the third mixture to form a fourth mixture; and adding and mixing a weighting additive into the fourth mixture to form the oil-based drilling fluid.

12. The method of claim 11, where the magnesium adamantane carboxylate compound is prepared by:

mixing a magnesium salt and a diamondoid compound having at least one carboxylic acid moiety to form a reactant mixture; and hydrothermally treating the reactant mixture at a reaction temperature for a reaction time to form the magnesium adamantane carboxylate salt.

13. The method of claim 12, where the magnesium salt and the diamondoid compound are mixed in amounts that provide a ratio of $Mg^{2+}$ to diamondoid compound in the reaction mixture of from 0.5:1 to 1.0:1.

14. The method of claim 12, where the magnesium salt is $Mg(OH)_2$.

15. The method of claim 12, where the reaction temperature is from 100° C. to 180° C.

16. The method of claim 12, where the magnesium adamantane carboxylate salt comprises a layered morphology.

17. The method of claim 11, where the oil-based drilling fluid comprises from 0.1 wt.% to 1.0 wt.% rheology modifier, based on the total weight of the oil-based drilling fluid.

18. A method for drilling in a subterranean formation under high-pressure high-temperature conditions, the method comprising:

providing or using in the drilling of a wellbore into the subterranean formation an oil-based drilling fluid, the oil-based drilling fluid comprising:

a base oil continuous phase;

an aqueous discontinuous phase; and at least one rheology modifier, the at least one rheology modifier comprising a magnesium adamantane carboxylate compound.

19. The method of claim 18, where the high-pressure high-temperature conditions comprise a wellbore pressure greater than 10,000 psi and a wellbore temperature greater than 300° F.

* * * * *